United States Patent
Anderson et al.

(10) Patent No.: US 10,844,414 B2
(45) Date of Patent: Nov. 24, 2020

(54) METHODS FOR PRODUCING STEVIOL GLYCOSIDES IN ENGINEERED YEAST

(71) Applicant: Cargill, Incorporated, Wayzata, MN (US)

(72) Inventors: James C. Anderson, Eden Prairie, MN (US); Ting Liu Carlson, Marietta, SC (US); Arlene M. Fosmer, Eden Prairie, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 15/750,636

(22) PCT Filed: Aug. 8, 2016

(86) PCT No.: PCT/US2016/046072
§ 371 (c)(1),
(2) Date: Feb. 6, 2018

(87) PCT Pub. No.: WO2017/024313
PCT Pub. Date: Feb. 9, 2017

(65) Prior Publication Data
US 2018/0230504 A1 Aug. 16, 2018

Related U.S. Application Data

(60) Provisional application No. 62/201,941, filed on Aug. 6, 2015.

(51) Int. Cl.
| C12P 19/56 | (2006.01) |
| A23L 27/30 | (2016.01) |
| C12N 1/16 | (2006.01) |

(52) U.S. Cl.
CPC ............... *C12P 19/56* (2013.01); *A23L 27/36* (2016.08); *C12N 1/16* (2013.01)

(58) Field of Classification Search
None
See application file for complete search history.

(56) References Cited

U.S. PATENT DOCUMENTS

| 2002/0164700 A1 | 11/2002 | Andersen et al. |
| 2006/0083838 A1 | 4/2006 | Jackson et al. |
| 2006/0134742 A1 | 6/2006 | Brazeau et al. |
| 2010/0184133 A1 | 7/2010 | Norgaard et al. |
| 2011/0081697 A1 | 4/2011 | Liu et al. |
| 2011/0189717 A1 | 8/2011 | Ajikumar et al. |
| 2012/0164678 A1 | 6/2012 | Stephanopoulos et al. |
| 2012/0165562 A1 | 6/2012 | Hattendorf et al. |
| 2013/0071339 A1 | 3/2013 | Markosyan et al. |
| 2013/0171328 A1 | 7/2013 | Kishore et al. |
| 2014/0329281 A1* | 11/2014 | Houghton-Larsen .................. C12N 9/0071 435/78 |
| 2014/0357588 A1 | 12/2014 | Markosyan et al. |
| 2015/0031868 A1* | 1/2015 | Lehmann .................. A23L 2/60 536/18.1 |
| 2015/0037462 A1 | 2/2015 | Markosyan et al. |
| 2016/0102331 A1 | 4/2016 | Boer et al. |
| 2016/0153017 A1 | 6/2016 | Van Der Hoeven et al. |
| 2016/0177360 A1 | 6/2016 | Boer et al. |
| 2016/0348192 A1 | 12/2016 | Tilloy et al. |
| 2018/0073050 A1 | 3/2018 | Boer et al. |
| 2018/0148750 A1 | 5/2018 | Anderson et al. |
| 2018/0155751 A1 | 6/2018 | Anderson et al. |
| 2018/0163244 A1 | 6/2018 | Anderson et al. |

FOREIGN PATENT DOCUMENTS

| EP | 1305440 | 6/2010 |
| WO | WO0125467 | 4/2001 |
| WO | WO2006045023 | 4/2006 |
| WO | WO2009140394 | 11/2009 |
| WO | WO2011153378 | 12/2011 |
| WO | WO2013022989 | 2/2013 |
| WO | WO2013096420 | 6/2013 |
| WO | WO2013110673 | 8/2013 |
| WO | 2014122227 A2 | 8/2014 |
| WO | WO2014122328 | 8/2014 |
| WO | WO2014145521 | 9/2014 |
| WO | WO2014191580 | 12/2014 |
| WO | WO2014191581 | 12/2014 |
| WO | WO2014193888 | 12/2014 |
| WO | WO2014193934 | 12/2014 |
| WO | WO2015007748 | 1/2015 |
| WO | WO2015011209 * | 1/2015 |
| WO | WO2015014959 | 2/2015 |
| WO | WO2015014969 | 2/2015 |
| WO | WO2016196321 | 12/2016 |
| WO | WO2016196345 | 12/2016 |
| WO | WO2016196368 | 12/2016 |

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Jasmin, et al., "The yield of experimental yeast populations declines during selection", Proc Biol Sci. 2012, vol. 279 (1746), p. 4382-8.
Jules, et al., "Two Distinct Pathways for Trehalose Assimilation in the Yeast *Saccaromyces cerevisiae*", Appl Environ Microbiol. May 2004, vol. 70(5): p. 2771-2778.
Chisti, Y. "Fermentation (Industrial): Basic Considerations" in: "Encyclopedia of Food Microbiology" (1999 ed.), pp. 663-674 (1999).

(Continued)

*Primary Examiner* — Christian L Fronda
(74) *Attorney, Agent, or Firm* — McDonnell Boehnen Hulbert & Berghoff LLP

(57) ABSTRACT

Disclosed are methods for producing steviol glycosides, such as rebaudioside D and rebaudioside M, using engineered yeast. The methods include growing yeast on non-fermentative carbon sources. Other methods include growing yeast on one or more polysaccharides in which saccharification and fermentation of the polysaccharides occurs simultaneously.

16 Claims, No Drawings
Specification includes a Sequence Listing.

(56) References Cited

OTHER PUBLICATIONS

International Search Report issued by the International Searching Authority for International Application No. PCT/US2016/034728, dated Sep. 8, 2016 (4 pages).
Non-Final Office Action issued in U.S. Appl. No. 15/578,125; dated May 21, 2019, pp. 1-14.
International Search Report issued by the International Searching Authority for International Application No. PCT/US2016/034781, dated Aug. 29, 2016 (4 pages).
Non-Final Office Action issued in U.S. Appl. No. 15/578,154; dated Jul. 16, 2019, pp. 1-12.
International Search Report issued by the International Searching Authority for International Application No. PCT/US2016/034826, dated Sep. 13, 2016 (4 pages).
International Search Report issued by the International Searching Authority for International Application No. PCT/US201616/046072, dated Dec. 1, 2016 (4 pages).
"Nomenclature committee of the international union of biochemistry and molecular biology (NC-IUBMB), Enzyme Supplement 5 (1999)," Eur J Biochem. 264(2):610-50, (1999).
Anderlei et al., "Device for sterile online measurement of the oxygen transfer rate in shaking flasks," Biochemical Engineering Journal 3478:1-6, (2000).
Barrett, "Nomenclature Committee of the International Union of Biochemistry and Molecular Biology (NC-IUBMB). Enzyme nomenclature. Recommendations 1992. Supplement 2: corrections and additions (1994)," Eur. J. Biochem., 232:1-6, (1995).
Barrett, "Nomenclature Committee of the International Union of Biochemistry and Molecular Biology (NC-IUBMB). Enzyme nomenclature. Recommendations 1992. Supplement 3: corrections and additions (1995)," Eur J Biochem. 237 (1):1-5 (1996).
Barrett, "Nomenclature Committee of the International Union of Biochemistry and Molecular Biology (NC-IUBMB). Enzyme Nomenclature. Recommendations 1992. Supplement 4: corrections and additions (1997)," Eur J Biochem. 250(1)1-6 (1997).
Chen et al., "The glucose RQ-feedback control leading to improved erythromycin production by a recombinant strain Saccharopolyspora erythraea ZL1004 and its scale-up to 372-m(3) fermenter," Bioprocess Biosyst Eng. 38(1):105-12 (2015).
Li et al., "Phylogenetic analysis of the UDP-glycosyltransferase multigene family of *Arabidopsis thaliana*," J Biol Chem. 276(6):4338-43 (2001).
Lynd, et al., "Microbial cellulose utilization: fundamentals and biotechnology," Microbial. Mol. Biol. Rev., 66:506-577 (2002).
Ohta et al., "Characterization of Novel Steviol Glycosides from leaves of Stevia rebaudiana Morita", Journal of Applied Glycoscience, The Japanese Society of Applied Glycoscience, Aug. 17, 2010, Issue 57, pp. 199-209.
Prakash et al., "Catalytic hydrogenation of the sweet principles of Stevia rebaudiana, Rebaudioside B, Rebaudioside C and Rebaudioside D and sensory evaluation of their reduced derivatives," Int J Mol Sci. 13(11):15126-36 (2012).
Prakash et al., "Isolation, characterization and sensory evaluation of a Hexa beta-D-glucopyranosyl diterpene from Stevia rebaudiana," Nat Prod Commun. 8(11):1523-6 (2013).
Tipton, "Nomenclature Committee of the International Union of Biochemistry and Molecular Biology (NC-IUBMB). Enzyme nomenclature. Recommendations 1992. Supplement: corrections and additions," Eur J Biochem., 223(1):1-5 (1994).
Verduyn, C. et al., "Effect of benzoic acid on metabolic fluxes in yeasts: a continuous-culture study on the regulation of respiration and alcoholic fermentation," Yeast 8, 501-517 (1992).

International Preliminary Report on Patentability from then International Search Authority for International Application No. PCT/US2016/034728; dated Dec. 5, 2017, pp. 1-14.
Extended European Search Report and Opinion issued by the European Patent Office for European Application No. 16804137.4, dated Sep. 14, 2018 (pp. 1-8).
International Preliminary Report on Patentability from then International Search Authority for International Application No. PCT/US2016/034781; dated Aug. 3, 2016, pp. 1-9.
Extended European Search Report and Opinion issued by the European Patent Office for European Application No. 16804152.3, dated Nov. 6, 2018 (pp. 1-4).
Supplementary European Search Report and Opinion issued by the European Patent Office for European Application No. 168041523, dated Oct. 25, 2018 (pp. 1-2).
International Preliminary Report on Patentability from then International Search Authority for International Application No. PCT/US20161034826; dated Aug. 20, 2017, pp. 1-13.
Extended European Search Report and Opinion issued by the European Patent Office for European Application No. 16804170.5, dated Dec. 10, 2018 (p. 1).
International Preliminary Report on Patentability from then International Search Authority for International Application No. PCT/US201616/046072; dated Feb. 6, 2018, pp. 1-12.
Extended European Search Report and Opinion issued by the European Patent Office for European Application No. 16834005.7, dated Feb. 13, 2019 (pp. 1-11).
Brandle & Telmer, "Steviol glycoside biosynthesis," Phytochemistry 68(14):1855-63 (2007).
Coelho, "Yarrowia lipolytica: An industrial workhorse," Current Research, Technology and Education Topics in Applied Microbiology and Microbial Biotechnology A. Méndez-Vilas (Ed.), 930-944 (2010).
Gonçalves, "Yarrowia Lipolytica and Its Multiple Applications in the Biotechnological Industry," The Scientific World Journal, vol. 2014, 1-14 (2014).
Kebabci et al., "Comparison of three Yarrowia lipolytica strains for lipase production: NBRC 1658, IFO 1195, and a local strain" Turk J Biol, 36 (2012) 15-24 (2012).
Kumar et al., "A comprehensive analysis of fifteen genes of steviol glycosides biosynthesis pathway in Stevia rebaudiana (Bertoni)" Gene 492:276-84 (Epub Oct. 20, 2011).
Moeller et al., "Optimization of Citric Acid Production from Glucose by Yarrowia lipolytica," Eng. Life Sci, 7(5):504-511 (2007).
Final Office Action issued in U.S. Appl. No. 15/578,125; dated Oct. 8, 2019, pp. 1-16.
Non-Final Office Action issued in U.S. Appl. No. 15/578,179; dated Dec. 23, 2019, pp. 1-9.
International Search Report and Written Opinion issued by the International Searching Authority for International Application No. PCT/EP2014/065858, dated Oct. 20, 2014 (12 pages).
International Preliminary Report on Patentability from the International Search Authority for International Application No. PCT/EP2014/065858, dated Jan. 1, 2016 (9 pages).
Examination Report issued by the European Patent Office for European Application No. 14741925.3, dated Mar. 14, 2017 (pp. 1-10).
Examination Report issued by the European Patent Office for European Application No. 14741925.3, dated Feb. 26, 2018 (pp. 1-3).
Non-Final Office Action issued in U.S. Appl. No. 14/906,497; dated Jul. 17, 2018 pp. 1-30.

* cited by examiner

METHODS FOR PRODUCING STEVIOL GLYCOSIDES IN ENGINEERED YEAST

This application is a national phase application of PCT/US2016/046072, filed Aug. 8, 2016, and entitled FERMENTATION METHODS FOR PRODUCING STEVIOL GLYCOSIDES, which claims the benefit of U.S. Provisional Patent Application No. 62/201,941, filed Aug. 6, 2015, and entitled FERMENTATION METHODS FOR PRODUCING STEVIOL GLYCOSIDES, each of which is hereby incorporated herein by reference in its entirety. The entire contents of the ASCII text file entitled "CAR0217P1_Sequence_Listing.txt," created on May 7, 2015 and having a size of 95 kilobytes, are incorporated herein by reference in their entirety. CAR0217WO Sequence Listing.txt created Aug. 6, 2016 is also filed herewith and incorporated herein by reference.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

Stevia is a genus of about 240 species of herbs and shrubs in the sunflower family (Asteraceae), native to subtropical and tropical regions from western North America to South America. The species Stevia rebaudiana, commonly known as sweetleaf, sweet leaf, sugarleaf, or simply stevia, is widely grown for its sweet leaves. Stevia-based sweeteners may be obtained by extracting one or more sweet compounds from the leaves. Many of these compounds are steviol glycosides, which are glycosides of steviol, a diterpene compound. These diterpene glycosides are about 150 to 450 times sweeter than sugar.

Examples of steviol glycosides are described in WO 2013/096420 (see, e.g., listing in FIG. 1); and in Ohta et. al., "Characterization of Novel Steviol Glycosides from Leaves of Stevia rebaudiana Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2a-2k. See also PCT Patent Publication WO 20013/096420.

Typically, on a dry weight basis, the four major steviol glycosides found in the leaves of Stevia are dulcoside A (0.3%), rebaudioside C (0.6-1.0%), rebaudioside A (3.8%) and stevioside (9.1%). Other glycosides identified in Stevia extract include one or more of rebaudioside B, D, E, F, G, H, I, J, K, L, M, N, O, steviolbioside and rubusoside.

While the major steviol glycoside Reb A is commonly used as sweetener in beverage applications, it has off-taste issues. More recently, there has been focus on certain minor steviol glycosides which have better taste properties. For example, rebaudioside M has higher sweetness intensity and is more potent than other steviol glycosides (e.g., see Prakash, I., et al. (2013) Nat. Prod. Commun., 8: 1523-1526, and WO 2013/096420). Rebaudioside D tastes about 200-220 times sweeter than sucrose and in a sensory evaluation it had a slow onset of sweetness and was very clean (e.g., see Prakash, I., et al. (2012) Int. J. Mol. Sci., 13:15126-15136).

Molecular techniques have been used to prepare recombinant organisms capable of synthesizing steviol glycosides via fermentation. For example, recombinant strains of Saccharomyces cerevisiae having multiple transgenes encoding enzymes involved in steviol glycoside synthesis have been used for the production of rebaudioside M and rebaudioside D (see, for example, WO2014/222227).

Saccharomyces cerevisiae typically ferments in the presence of >1-2 g/l glucose in the media (Crabtree effect). When this occurs, ethanol is produced as a fermentation product. Ethanol production reduces the biomass and the desired bioproduct (e.g. steviol glycosides). One approach of keeping glucose limited and/or using a substrate that does not stimulate the Crabtree effect may be to use non-fermentative substrates that can support steivol glycoside production. Another approach to limit glycose release and keep glucose levels below those that simulate fermentation in yeast is by the application of simultaneous saccharification and fermentation (SSF).

SUMMARY

Disclosed are methods of producing steviol glycosides by growing yeast on non-fermentative substrates. Also disclosed is a method of growing yeast to produce steviol glycosides by the simultaneous saccharification and fermentation.

A method for producing steviol glycoside(s) in accordance with one aspect comprises growing engineered yeast capable of producing one or more steviol glycoside(s) in a glucose-limited medium that contains carbohydrates fermentable by the engineered yeast. Less than 50% by weight (wt %), preferably <20 wt %, more preferably <10 wt % or <5 wt %, of the fermentable carbohydrates are glucose and/or fructose, i.e., glucose, fructose, or glucose and fructose. In some aspects, the glucose and/or fructose may comprise less than 2 wt %, preferably <1 wt %, of the fermentable carbohydrates and in one useful aspect the glucose-limited medium is substantially glucose-free. At least 50 wt %, preferably at least 60 wt %, at least 70 wt %, at least 80 wt %, at least 90 wt %, or at least 95 wt % of the fermentable carbohydrates are selected from the group consisting of raffinose, mannose, trehalose, galactose, maltose, glycerol, and combinations thereof, preferably selected from the group consisting of raffinose, mannose, trehalose, galactose, and combinations thereof, more preferably selected from the group consisting of raffinose, mannose, trehalose, and combinations thereof.

A method for producing steviol glycoside(s) in another aspect comprises:
 (a) providing an engineered yeast capable of producing one or more steviol glycoside(s) and a carbon source having one or more polysaccharides and/or one or more oligosaccharides;
 (b) converting at least a portion of the one or more polysaccharides and/or one or more oligosaccharides into one or more monosaccharides; and
 (c) growing the engineered yeast on the one or more monosaccharides to produce one or more steviol glycoside(s).

DETAILED DESCRIPTION

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Fermentation methods of the disclosure use engineered yeast capable of producing steviol glycosides. An engineered yeast capable of producing steviol glycosides can include one or more exogenous nucleic acids that encode enzyme(s) that promote formation of one or more steviol glycosides in the cell.

As used herein, the term "steviol glycoside(s)" refers to glycosides of steviol. Exemplary steviol glycoside, include, but are not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, stevioside, steviolbioside, dulcoside A, and rubusoside. Engineered yeast can produce steviol glycosides that are the same as steviol glycosides found in nature ("naturally occurring") as well as steviol glycosides that are not known to exist in *Stevia rebaudiana* leaves. Steviol glycosides can be formed in an engineered yeast by enzymatic processes.

Structurally, steviol glycosides have a central molecular moiety, which is a single steviol base, and glucopyranosyl residues attached to the C13 and/or C19 atoms of the steviol base, according to the atom numbering on the base shown below. That is, glucopyranosyl residues represent groups $R_2$ and $R_1$ in the following formula:

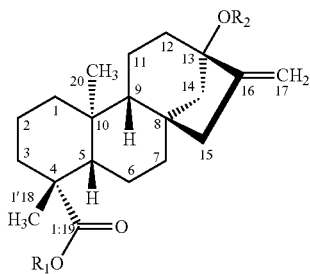

According to the current disclosure, steviol glycosides are produced in a process having at least two phases: first and second phases where a glucose-containing feed composition is provided to the medium in different modes of feeding in each phase, such as variable feeding and then constant feeding. A two phase feeding process as described herein can result in a growth rate that is slower in the second phase than in the first phase, and consequently increased steviol glycoside production rates, reduced fermentation times, and reduced biomass concentrations. The engineered yeast can have a set of enzymes that provide a pathway for the synthesis of steviol glycosides. For example, the process can produce steviol glycosides such as RebM and RebD.

The method of the disclosure can use various yeast host cells engineered to provide a pathway to one or more steviol glycosides. Such cells can be transformed with one or more DNA construct(s) encoding enzymes for steviol glycoside synthesis. Exemplary yeast that can be used for hosts for exogenous DNA constructs encoding steviol glycoside pathway enzymes, include, but are not limited to species of *Candida, Kloeckera (Hanseniaspora), Kluyveromyces, Lipomyces, Pichia (Hansenula), Rhodotorula, Saccharomycete, Saccharomyces, Schizosaccharomyces, Torulopsis, Torulaspora, Yarrowia,* and *Zygosaccharomyces*. Exemplary species are *Candida albicans, Pichia pastoris, Saccharomyces cerevisiae, Schizosaccharomyces pombe,* and *Yarrowia lipolytica*. Further, host cells can also include genetic modifications other than those of the steviol glycoside pathway that may provide improved performance during fermentation.

An "engineered yeast" refers to yeast cells having at least one exogenous DNA sequence that is introduced into the cell, either integrated into the cell's genome or present on an extrachromosomal construct, such as a plasmid or episome. The term "exogenous" refers to a molecule, such as a nucleic acid, or an activity, such as an enzyme activity, that is introduced into the host yeast. An exogenous nucleic acid can be introduced into the yeast host by well-known techniques and can be maintained external to the host's chromosomal material (e.g., maintained on a non-integrating vector), or can be integrated into the yeast's chromosome, such as by a recombination event. Generally, the genome of an engineered yeast is augmented through the stable introduction of one or more recombinant genes. An exogenous nucleic acid can encode an enzyme, or portion thereof, that is either homologous or heterologous to the yeast. An exogenous nucleic acid can be in the form of a "recombinant gene or DNA construct" referring to a nucleic acid that is in one or more ways manipulated through molecular techniques to be in a form that does not naturally exist.

The term "heterologous" (e.g., "non-native") refers to a molecule or activity that is from a source that is different than the referenced molecule or organism. Accordingly, a gene or protein that is heterologous to a referenced organism is a gene or protein not found in that organism. In the context of the disclosure, a "heterologous glycosyltransferase" refers to a glycosyltransferase polypeptide that is different from any glycosyltransferase polypeptide that may be native to the host organism. For example, a specific glycosyltransferase gene found in a first species and exogenously introduced into a host yeast organism that is different than the first species is "heterologous" to the host yeast.

The engineered yeast can use an auxotrophic marker suitable for selecting for a transformant having a nucleic acid encoding a steviol glycoside pathway enzyme. The host yeast can include modifications (deletions, etc.) in one or more genes that control auxotrophies, such as LYS2, LEU2, HIS3, URA3, URA5, and TRP1. Using a host cell having a desired genetic background for introduction of one or more exogenous genes, one or more gene construct(s) is introduced into a cell to integrate into the genome, or to be stably maintained and allow for expression. Methods for introducing a gene construct into a host cell include transformation, transduction, transfection, co-transfection, and electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein, or the production of a bioproduct such as a steviol glycoside.

The transformation of exogenous nucleic acid sequences including the steviol pathway genes can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of the introduced nucleic acid sequences or their corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The terpenoid compounds isopentenyl diphosphate (IPP) and dimethylallyl diphosphate (DMAPP) can serve as chemical precursors to steviol glycosides in an engineered yeast. Some organisms, including plants, insect, and some microbial species, have a mevalonate (MVA) pathway that converts acetyl-CoA through a series of chemical intermediates to IPP and DMAPP. Some organisms produce IPP and DMAPP through the non-mevalonate pathway (also known as the methyl D-erythritol 4-phosphate or MEP pathway) starting with glyceraldehyde-3-phosphate (G3P) and pyruvate (PYR).

The yeast *Saccharomyces cerevisiae* naturally expresses genes of the mevalonate pathway. Mevalonate pathway genes include: (a1) acetoacetyl CoA thiolase (EC 2.3.1.9), (b1) 3-hydroxy-3-methylglutaryl-coenzyme A (HMG-CoA) synthase (EC 4.1.3.5); (c1) HMG-CoA reductase (EC 1.1.1.34); (d1) mevalonate kinase (EC 2.7.1.36); (e1) phosphomevalonate kinase (EC 2.7.4.2); and (f1) mevalonate diphosphate decarboxylase (EC 4.1.1.33). Enzymes of the mevalonate pathway convert acetyl-CoA to IPP as follows: acetyl-CoA→acetoacetyl-CoA→3-hydroxy-3-methylglutaryl-CoA→mevalonate→mevalonate-5-phosphate→mevalonate-5-pyrophosphate→IPP.

In some embodiments, the engineered yeast can include one or more modifications to increase the flux from acetyl-CoA to IPP and/or DMAPP, thereby providing an increased pool of IPP and/or DMAPP for use in a pathway to steviol. The modifications can include, for example, increasing expression or activity of one or more mevalonate pathway enzymes (a1)-(f1), such as by placing a nucleic acid encoding an enzyme that is homologous or heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a higher level of enzymatic activity as compared to the native enzyme.

Alternatively, the non-mevalonate (MEP) pathway can be used to provide IPP and DMAPP as precursors to steviol glycoside production. The yeast *Saccharomyces cerevisiae* do not naturally express genes of the MEP pathway, but can optionally be engineered to provide MEP pathway genes. Theoretically, the MEP pathway is more energetically efficient generally because it loses less carbon as $CO_2$ as compared to the MVA pathway (MEP pathway: 1 $CO_2$/IPP; MVA pathway: 4 $CO_2$/IPP; sugar as carbon source).

In particular, in the non-mevalonate (MEP) pathway compounds isopentenyl diphosphate (IPP), dimethylallyl diphosphate (DMAPP) are generated through a series of intermediates leading from glyceraldehydes-3-phosphate (G3P) and pyruvate (PYR), and a number of enzymes are responsible for this conversion. Enzymes involved in a biosynthetic pathway from G3P and PYR to IPP and DMAPP include (a2) 1-deoxy-D-xylulose-5-phosphate synthase (DXS), (b2) 1-Deoxy-D-xylulose-5-phosphate reductoisomerase (ispC)-, (c2) 4-diphosphocytidyl-2C-methyl-D-erythritol synthase (IspD), (d2) 4-diphosphocytidyl-2-C-methyl-D-erythritol kinase (IspE), (e2) 2C-Methyl-D-erythritol-2,4-cyclodiphosphate Synthase (IspF), (f2) l-hydroxy-2-methyl-2-(E)-butenyl-4-diphosphate synthase (IspG), (g2) 4-hydroxy-3-methyl-2-(E)-butenyl-4-diphosphate reductase (IspH), and (h2) isopentenyl-diphosphate isomerase (IDI).

The methods of the disclosure for producing steviol glycoside(s) by fermentation can use engineered yeast that have one or more genetic modifications to increase the flux from G3P and PYR to IPP and/or DMAPP, thereby providing an increased pool of IPP and/or DMAPP for use in a pathway to steviol. The modifications can include, for example, increasing expression or activity of one or more enzymes (a2)-(h2), such as by placing a nucleic acid encoding an enzyme that is heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a high levels of enzymatic activity.

The methods of the disclosure for producing steviol glycoside(s) by fermentation can use engineered yeast can also include a pathway to convert IPP and/or DMAPP to steviol. For example, in some aspects the engineered yeast can include exogenous nucleic acids expressing the following enzymes: (a3) geranyl geranyldiphosphate synthase (GGPPS), (b3) copalyl diphosphate synthase (CPS), (c3) kaurene synthase (KS), (d3) kaurene oxidase (KO), and (e3) kaurenoic acid 13-hydroxylase (KAH). Enzymes of the mevalonate pathway converts IPP and/or DMAPP to steviol as follows: IPP/DMAPP→geranyl geranyldiphosphate→copalyl diphosphate→kaurene→kaurenoic acid→steviol. Exogenous nucleic acids encoding enzymes (a3)-(e3) that are heterologous to the yeast cell can be placed under the control of a promoter that provides increased expression, using multiple copies of the nucleic acid, and/or using a variant enzyme (e.g., one including one or more amino acid substitutions), or a variant heterologous enzyme that provides a high levels of enzymatic activity.

The methods of the disclosure for producing steviol glycoside(s) by fermentation can use engineered yeast having any pathway to convert steviol to a steviol glycoside. If more than one steviol glycoside pathway enzymes are present in the engineered yeast, the yeast may be able to produce different steviol glycosides. For example, the yeast may be able to produce two, three, four, five, six, seven, eight, nine, ten, or more than ten different steviol glycoside species.

The steviol glycoside pathway can include one or more uridine diphosphate (UDP) glycosyltransferases (UGTs) that mediate the transfer of glycosyl residues from activated nucleotide sugars to acceptor molecules. In the case of a steviol glycoside pathway, a monosaccharide unit can be transferred to a hydroxyl or carboxyl moiety on a steviol or steviol glycoside molecule, or to a hydroxyl group on a glucose group that is attached to the steviol base. UGTs have been classified into families and subfamilies based on sequence homology. See Li, et al., 2001, J. Biol. Chem. 276:4338-4343. A superfamily of over 100 genes encoding UGTs, each containing a 42 amino acid consensus sequence, has been identified in the model plant *Arabidopsis thaliana*, and genes encoding UGTs have also been identified in several other higher plant species.

Exemplary UDP-glucosyltransferase can be any UDP-glucosyltransferase capable of adding at least one glucose unit to the steviol and or steviol glycoside substrate to provide the target steviol glycoside. In one embodiment, the engineered yeast can include one or more UDP-glucosyltransferase selected from group UGT74G1, UGT85C2, UGT76G1, UGT91D2, and also UGTs having substantial (>85%) identity to these polypeptides. An engineered yeast can include one or more exogenous nucleic acid molecule(s) that code for these UGTs.

The engineered yeast can also include one or more UGT and UDP-glucose recycling enzyme(s). An exemplary UDP-glucosyltransferase capable of adding at least one glucose unit to rubusoside to form stevioside is UGT91D2. An exemplary UDP-glucosyltransferase capable of adding at least one glucose unit to stevioside to form rebaudioside A is UGT76G1. An exemplary UDP-glucosyltransferase capable of adding at least one glucose unit to rebaudioside A to form rebaudioside D is UGT91D2. An exemplary UDP-glucosyltransferase capable of adding at least one glucose unit to rebaudioside D to form rebaudioside M is UGT76G1.

Exemplary publications that describe engineered microorganisms for steviol glycoside production and steviol glycoside pathway enzymes include, for example, US2014/0357588, WO2014/193934, WO2014/193888, and WO2014/222227, the entirety of each of which is incorporated herein by reference.

In one embodiment, an engineered yeast useful for the production of steviol glycosides expresses the following enzymes: geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91 d2, and a EUGT11. WO 2014/122227 describes an engineered yeast strain that express these enzymes. The UGT74G1 enzyme functions as a uridine 5'-diphospho glucosyl:steviol 19-COOH transferase and a uridine 5'-diphospho glucosyl: steviol-13-O-glucoside 19-COOH transferase. The UGT76G1 enzyme is a *stevia* uridine diphosphate dependent glycosyltransferase that catalyzes several glycosylation reactions on the steviol backbone. The UGT76G1 enzyme can catalyze glycosylation of steviol and steviol glycosides at the 19-O position or the 13-O position. The UGT91 D2 and EUGT11 enzymes can function as a uridine 5'-diphospho glucosyl: steviol-13-O-glucoside transferases (also referred to as a steviol-13-monoglucoside 1,2-glucosylase), transferring a glucose moiety to the C-2' of the 13-O-glucose of the acceptor molecule, steviol-13-O-glucoside, or as uridine 5'-diphospho glucosyl: rubusoside transferases transferring a glucose moiety to the C-2' of the 13-O-glucose of the acceptor molecule, rubusoside, to produce stevioside. The EUGT11 enzyme also can transfer a glucose moiety to the C-2' of the 19-O-glucose of the acceptor molecule, rubusoside, to produce a 19-O-1,2-diglycosylated rubusoside.

The term "medium" refers to a liquid composition in which the engineered yeast or fungus can be maintained, can grow, can ferment, or combinations thereof. A "medium" may also be referred to as a "broth" or "cell culture," and terms such as "growth," "division," "respiration," and "fermentation" may be used to more specifically define the type of cellular activity that is occurring in the medium.

A medium can be defined with regards to the components present in the medium, and amounts thereof, such as carbon sources, including (a) carbohydrates such as glucose and starch products such as maltodextrin; (b) nitrogen sources, such as yeast nitrogen base, ammonium hydroxide, urea, ammonium sulfate, or any combination thereof; (c) salts, such as potassium phosphate (monobasic, dibasic), magnesium sulfate, sodium chloride, and calcium chloride; (d) vitamins, such as biotin, calcium pantothenate, folic acid, (myo)-inositol, nicotinic acid, p-aminobenzoic acid, pyridoxine HCl, riboflavin, thiamine HCL, and chelator, citric acid; (e) trace metals such as boric acid, copper sulfate, cobalt chloride, calcium chloride, potassium iodide, ferrous sulfate, magnesium sulfate, manganese chloride, sodium molybdate, and zinc sulfate. Components in the medium can be defined on a dry weight basis. Further, the medium is water-based, or an "aqueous" composition. The medium can also be defined with regards to its pH, and biocompatible acids, bases, and buffers that are used to control the pH in the medium.

In one implementation, the glucose content in the glucose-limited medium is kept in the range of about 0 g/L to about 5 g/L, or 0 g/L to about 2 g/L, or less than 1 g/L. In exemplary aspects, the concentration of a nitrogen source (total amount) in the medium, such as yeast nitrogen base, ammonium hydroxide, urea, ammonium sulfate, is kept in the range of about 5 g/L to about 40 g/L. In exemplary aspects, the concentration of salts (total amount) in the second medium, such as salts including magnesium sulfate in the range of about 0 g/L to about 12 g/L, and potassium phosphate in the range of about 0 g/L to about 22 g/L. In exemplary aspects, the concentration of trace metals (total amount) in the second medium is kept in the range of about 0 g/L to about 0.4 g/L, or 0 g/L to about 0.2 g/L.

A composition (a "feed composition") can be added to the medium that includes the engineered yeast to increase the volume of the medium, and as the engineered yeast grows in the medium, the amount of biomass. The feed composition can include components for yeast growth and fermentation to form a desired medium. The feed composition can include a carbohydrate(s), a nitrogen source, such as ammonium hydroxide, urea, ammonium sulfate, or any combination thereof; salts, vitamins, and trace metals. The concentration of the components in the feed composition may be greater than the concentration of components in the medium so that when the feed composition is added it provides desired amounts of components in the medium suitable for fermentation of the engineered yeast.

Fermentation of the engineered yeast can be performed using starch and/or sugar containing plant material derivable from any plant and plant part, such as tubers, roots, stems, leaves and seeds. Starch and/or sugar-containing plant material can be obtained from cereal, such as barley, wheat, maize, rye, sorghum, millet, barley, potatoes, cassava, or rice, and any combination thereof. The starch- and/or sugar-containing plant material can be processed, such as by methods such as milling, malting, or partially malting. In some embodiments, the medium for growth and/or fermentation can include a treated starch, e.g., a partially hydrolyzed starch. The partially hydrolyzed starch can include high molecular weight dextrins and high molecular weight maltodextrins. A partially hydrolyzed starch product can be used that has amounts of starch and starch degradation products within desired ranges beneficial for steviol glycoside production.

Optionally, a starch degrading enzyme can be added to the medium that includes a starch material in order to increase the concentration of monomeric sugars such as glucose that can be utilized by the engineered yeast during the fermentation stage. Exemplary starch-degrading enzymes include amylolytic enzymes such as glycoamylase and amylase.

In one useful implementation, the medium is a glucose-limited medium that contains carbohydrates fermentable by the engineered yeast, and the concentration of glucose and/or fructose (i.e., glucose, fructose, or glucose and fructose) is limited. In the glucose-limited medium, the fermentable carbohydrates are than 50% by weight (wt %), preferably less than 20 wt %, more preferably less than 10 wt % or less than 5 wt %, glucose and/or fructose. The glucose-limited medium may be substantially free of glucose, substantially free of fructose, or substantially free of both glucose and fructose.

The glucose-limited medium includes an ethanol-limiting substrate that may be the primary carbon source for fermentation. The ethanol-limiting substrate selected from the group consisting of raffinose, mannose, trehalose, galactose, maltose, glycerol, and combinations thereof. In one preferred implementation, the ethanol-limiting substrate is selected from the group consisting of raffinose, mannose, trehalose, galactose, and combinations thereof. In another preferred implementation, the ethanol-limiting substrate is selected from the group consisting of raffinose, mannose, trehalose, and combinations thereof. In certain useful embodiments, the ethanol-limiting substrate is at least 95 wt % raffinose, mannose, or trehalose.

The ethanol-limiting substrate comprises at least 50 wt % of the fermentable carbohydrates in the glucose-limited medium. The ethanol-limiting substrate desirably comprises at least 60 wt % or at least 70 wt %, e.g., at least 80 wt %, at least 90 wt %, or at least 95 wt %, of the fermentable carbohydrates in the glucose-limited medium.

If so desired, the fermentable carbohydrates in the glucose-limited medium may include carbohydrates other than glucose, fructose, raffinose, mannose, trehalose, galactose, maltose, and glycerol. Depending on the feedstock employed, these sugars can include xylose, arabinose, cellobiose, or stachyose, for example.

In some optional modes of practice, fermentation can be carried out in medium that includes steviol-containing compounds. Such compounds can be directly used by the glucosyltransferases in the engineered yeast. For example, optionally, fermentation can be carried out in medium containing steviol-13-O-glucoside or steviol-19-O-glucoside. Using this medium, the microorganism may contain and express genes encoding a functional EUGT11, a functional UGT74G1, a functional UGT85C2, a functional UGT76G1, and a functional UGT91 D2. Compounds such as rebaudioside A, rebaudioside D, and rebaudioside M may be obtained from the fermentation medium. As another option, fermentation can be carried out in medium containing rubusoside. Using this medium, the microorganism may contain and express genes encoding a functional EUGT11, a functional UGT76G1, and a functional UGT91 D2. Compounds such as rebaudioside A, D, and M may be obtained from the medium following fermentation.

In some cases fermentation is carried out in industrial capacity fermenters in order to achieve commercial scale economic benefits and control. In an embodiment, the fermentation is carried out in a fermenter that has a capacity of about 10,000 liters or more.

The terms "first phase" and "second phase" (and optionally, "pre-phase," "third phase," "fourth phase," fifth phase," etc., if necessary) may be used to describe aspects of the method of producing steviol glycosides with regards to the medium. The term "stage" may also be used for "phase." The process includes two or more phases where the medium is treated differently in each phase, such as by adding a feed composition to the medium in a second, later, phase of the process in a mode that is different than a mode of adding the feed composition in the first, earlier, phase. The difference in mode of addition affects the growth of the engineered yeast, and production of the steviol glycosides during the process.

Prior to the first phase (in which cell growth is controlled by to the first mode of adding), the cells can be cultured according a "pre-phase." The pre-phase can be a "seed/initial growth phase" in which cells are grown in a medium to become acclimated to the medium components (carbohydrates, nitrogen source, salts, vitamins, trace metals). In the pre-phase carbohydrate supply to the cells is not modulated as it is during the first and second phases, so the cells may grow at their maximum biological rate. For example, the cells in the pre-phase may be batch fed. As the cells become acclimated to the medium, the cells will enter a growth phase and increase in cell numbers. During the pre-phase, the engineered yeast can multiply by budding, referred to as yeast division.

For example, during the pre-phase a growth composition that includes a carbohydrate(s), a nitrogen source, such as yeast nitrogen base, ammonium hydroxide, urea, ammonium sulfate, or any combination thereof; salts, vitamins, and trace metals can be added to medium that includes the engineered yeast in a batch process. In some modes of practice a composition is added to provide a medium that has ammonium hydroxide, urea, ammonium sulfate, or combinations thereof, as the sole nitrogen source. The same composition can be used as a feed composition in the subsequent first phase, where cell growth is controlled by the mode of addition of the feed composition to the medium.

Following the pre-phase, which is characterized by rapid cell growth and increase in biomass, the first phase (e.g., step a) can be commenced by regulating addition of the glucose containing composition according to the first mode of adding. The first phase can be described in various ways, such as by the how the feed solution is added to the medium and how the cells grow in response to that type of addition.

The mode of addition can affect the doubling times of the engineered yeast. The doubling times in the first phase can be greater (slower growth) than the doubling times in the pre-phase. During the first phase the biomass of the medium can increase, but it may increase at a rate that is lower than the increase seen in the pre-phase. The first phase can also be described in terms of how the cells grow as compared to the second phase, where feed solution is added to the medium in a second mode that is different than the first mode.

For example, in the first phase the yeast can be grown in a medium under conditions to achieve one or more growth rate(s) (dilution rate(s)) that are within a first range that is greater than growth in the second phase. For example, in the seed/growth phase the growth rate can be about 0.06 l/h or greater, such as a rate in the range of about 0.06 l/h to about 0.17 l/hr, or about 0.09 l/h to about 0.15 l/hr.

Optionally, the first phase can be described in terms of glucose concentration in the medium. For example, in some modes of practice, the first phase is started at a time when there is less than 3 g/L of glucose in the medium. For example, the amount of glucose in the medium during the pre-phase can be monitored and when the concentration drops below 3 g/L, the first phase feeding can be started.

A desired growth rate in the first phase can be achieved by adding a composition comprising glucose to the medium according to a first mode. A "mode of feeding" refers to a way a feed composition that includes glucose is added to the medium having the engineered yeast. Modes of feeding include constant rates of feeding, non-constant rates of feeding, continuous addition of feed composition, bulk addition of feed composition, etc. In some modes of feeding, a feed composition is added to the medium at a non-constant rate of feeding during the first phase. For example, the non-constant rate of feeding can be a variable rate of feeding.

A variable rate of feeding refers to adding a feed solution to the medium at two or more different rates over a period of adding a feed solution to the medium. In some modes of practice, during a variable rate feeding the rate decreases over a period of time. For example, in a growth phase of the process the feeding can change from a higher rate of feeding earlier in the growth phase to a lower rate of feeding later in the growth phase. This can be carried out by constantly decreasing rate of feeding, or can be carried out by a series of small decremental steps. In an optional mode of practice, a variable rate of feeding can include increasing the rate of feeding and then decreasing the rate of feeding.

A variable rate of feeding can be achieved using a variable rate addition system. Examples of such systems include a variable speed pump or a metering valve (such as a throttle valve) operably connected to a pump, which pump or valve can be utilized to vary the amount of feed composition introduced into the fermentation medium over time.

The first phase may also be explained with reference to one or more parameters associated with the medium, such as the period of time of the first phase, the temperature of the medium, the amount of biomass grown, and the pH of the medium. In some modes of practice, the first phase with a variable rate of feeding can be carried out for a period of time of about two hours or greater and up to about 40 hours. For example, the first phase can be about 10 hours or greater, such as a period of time in the range of about 10 hours to about 30 hours, or about 10 hours to about 24 hours. The first phase may encompass all or part of the lag phase of growth, and all or part of the log (exponential) phase of growth of the engineered yeast. After this period of time the mode of adding the feed composition including glucose to the medium can then be changed (e.g., to a constant rate of feeding in the second phase).

In exemplary modes of practice, in the first phase the medium is kept at a temperature in the range of about 25-35° C., or 28-32° C., and most preferably at about 30° C. Also, growth of the engineered yeast can be performed with aeration, and with agitation. Aeration conditions can have an effect on the amount of oxygen dissolved in the medium, and therefore the oxygen available to the engineered yeast. The amount of oxygen uptake by the engineered yeast can be controlled by the rate at which oxygen is supplied the formation of small oxygen bubbles in the medium, which can be achieved through agitation and/or sparging.

In the medium and during the first phase, the aeration can be performed. Aeration may be described in terms of dissolved oxygen transfer rate to the medium in units of mg $min^{-1}$ $liter^{-1}$. Aeration may also be described in terms of the dissolved oxygen (%). (For example, see Anderlei, T., and Büchs, J. (2000) Biochem. Engin. J. 3478:1-6). A sparging technique that promotes the formation of fine gas bubbles can be performed to provide desired aeration. In some modes of practice, during the first phase, agitation and aeration are increased, such as in a stepwise manner. Methods of the disclosure using a two phase feeding process can also reduce the aeration needs in the medium while still providing desired steviol glycoside production. In some modes of practice the dissolved oxygen is maintained at greater than 15%.

As used herein "biomass" refers to the weight of the engineered yeast, which can be measured in grams of dried cell weight per liter of medium (DCW/L). As another exemplary parameter, in some modes of practice, the first phase with a variable rate of feeding produces an amount of biomass of at least about 5 dcw/L. Preferably, the amount of biomass produced is in the in the range of about 5 g dcw/L to about 60 g dcw/L, about 20 g dcw/L to about 60 g dcw/L, or about 20 g dcw/L to about 40 g dcw/L.

As another example, in some modes of practice, the first phase with a variable rate of feeding is carried out at a pH of less than 6.0 or less, less than about 5.5, and preferably less than 5.2, such as in the range of about 4.0 to about 5.2. During the first phase the pH can be monitored to so that it stays within a desired, lower pH range, such as in the range of about 4.0 to 5.2. Acid or base can be added to the medium during the feeding to maintain the pH within a desired range.

After the first phase, the engineered yeast can enter the second phase, such as a "fermentation phase" where the mode of providing the feed composition is different than in the first phase. In the second phase the growth of the engineered yeast has at least slowed and is actively assimilating carbohydrate and producing steviol glycoside(s). As used herein "fermentation" is used to describe the phase of significant production of steviol glycoside(s), which can occur in fully aerobic, partially aerobic or anaerobic conditions. In partially aerobic conditions, both fermentative and respiratory pathways can be active, and some cell growth may occur. In partially aerobic conditions the amount of oxygen consumed can be less than during the seed/growth phase.

In the second phase, a feed composition with glucose can be added to the medium in a different mode than in the first phase. In, some modes of practice, the first and second phases are carried out in the same vessel, wherein during the first phase a feed solution that includes glucose is added to the medium in the vessel at a variable rate, and then in the second phase the feed solution is added to the medium in the same vessel but at a constant rate.

In some modes of practice, in the second phase the feed composition is added to the medium at a constant feeding rate. For example, the constant rate of feeding is not greater than 10 g glucose/L media/h, and preferably at a constant rate of feeding in the range of 2 g glucose/L media/h to 10 g glucose/L media/h.

For example, in the second phase which includes fermentation and production of the steviol glycosides, the yeast can be grown in a medium under conditions to achieve one or more growth rate(s) that are within a range. For example, in the second phase the growth rate(s) can be about 0.09 l/h or less, such as a rate in the range of about 0.015 l/h to about 0.09 l/hr, or about 0.015 l/h to about 0.06 l/hr. In some embodiments, the growth rate (dilution rate) in step (b) is in the range of 50-90% of a maximum growth rate (dilution rate) in step (a). In some embodiments, the growth rate (dilution rate) in step (b) is in the range of 50-100% of a maximum growth rate (dilution rate) in step (a).

In some modes of practice, in the second phase with a constant rate can be carried out for a period of time to provide desired production of steviol glycosides. For example, the second phase can be started at a time of about 30 hours or later from the start of step (a), and then can be performed up to 130 hours from an from the start of step (a). The second phase may encompass all or part of the fermentation phase where the majority of steviol glycosides are produced. Preferably most of the steviol glycoside(s) (i.e., greater than 50%) are produced by the engineered yeast during the second phase. Methods of the disclosure including the two phase feeding provide a benefit with regards to fermentation, allowing up to about a 25% reduction, or even up to a 40% reduction in fermentation times as compared to a control process (e.g., a single phase fermentation).

Further, in some modes of practice, in the second phase with a constant rate of feeding can be controlled so the engineered yeast do not grow to a biomass amount of greater than 180 g dcw/L. Methods of the disclosure including the two phase feeding provide a benefit with regards to biomass production, allowing up to about a 25% reduction in the amount of biomass produced as compared to a control process with a single phase fermentation.

Further, in some modes of practice, during the second phase the medium can have a higher pH than the pH in the medium during the first phase. For example, at the start of, or during the second phase, a base can be added to the medium to increase the pH from a lower to a higher pH. The base can be present in the feed composition, or can be added separate from the feed composition for the second phase. For example, in the second phase the pH can be adjusted to about pH 5.8 or greater, or about pH 6.0 or greater, such as in the range of about pH 5.8 to about pH 7.5 or greater, or about pH 6.0 to about pH 7.0. During the second phase, the pH can be monitored (e.g., periodically or continuously) and adjustments to the medium can be made if the pH falls outside a desired range. For example, ammonium hydroxide can be added to the second medium if the pH drops below 6.0 or 5.8, so as to adjust the pH to about 6.0 or greater.

In exemplary modes of practice, fermentation and optionally growth in the second medium is performed at a temperature in the range of about 25-35° C., or 28-32° C., and most preferably at about 30° C. Also, fermentation and optionally growth of the engineered yeast in the second medium can be performed with aeration, and with agitation. Methods of the disclosure using a two phase feeding process can also reduce the aeration needs in the medium while still providing desired steviol glycoside production.

During fermentation, the medium can be monitored for the production of steviol glycosides. Fermentation can be stopped at a point where there is a desired steviol glycoside total amount and profile.

The "total steviol glycosides" refers all the steviol glycosides present in the medium after a period of fermentation, which includes the amount of steviol glycosides in the liquid medium and obtainable from the engineered yeast. The steviol glycoside content can be expressed with regards to a total steviol glycosides amount in the medium, or the amount of one or more, but not all, steviol glycosides, in the medium. The amount of steviol glycosides in the composition can be expressed in relation to one another, or to the total amount of steviol glycosides, such as by a weight percentage of the total amount of steviol glycosides, or a ratio, or range of ratios, expressed as weight percent, or molar percent. The amount of steviol glycosides can also be expressed relative to a control sample, such as a control sample prepared by a process that does not include the first and second stages of feeding.

In some modes of practice, method of the disclosure provides improvement in the production of certain steviol glycosides, such as rebaudioside D and rebaudioside M.

Methods of the disclosure can provide an improvement in the rate of steviol glycoside production during fermentation. For example, engineered yeast that are grown and fermented the first and second phase method as described herein can exhibit an increase in the rate of steviol glycoside production that is about 1% or greater, about 2% or greater, about 3% or greater, and up to about 15% or about 12%, relative to the rate of steviol glycoside production engineered yeast strain that is grown and fermented in a control process.

The phased feeding according to the disclosure can result in Reb D and Reb M production and increased production rates, reduced fermentation times and reduced biomass concentrations.

Following the second phase wherein fermentation produces steviol glycoside(s), a composition containing one or more steviol glycoside(s) can be obtained from the medium using various techniques. In some embodiments, a compound such as permeabilizing agent can be added to the medium to enhance removal of the steviol glycosides from the cell and into the medium.

The medium can then be centrifuged or filtered to remove the engineered cells. The medium can optionally be treated to remove low molecular weight components (glucose, basic nutrients, and salts), such as by membrane dialysis. Depending on a desired use, a composition comprising one or more steviol glycoside compound(s) can be used.

After fermentation the engineered yeast can optionally be treated using a heat treatment method to enhance the recovery of steviol glycosides. After fermentation, but before any heat, treatment the medium may contain a suboptimal amount of the steviol glycosides, with the most of the desired steviol glycosides within the engineered yeast. To increase the recovery of steviol glycosides, in some modes of practice a composition, such as the medium at the higher pH in which the engineered yeast have been fermented, is heated to a temperature in the range from 50° C. to 95° C., or 70° C. to 95° C., for a period of time in the range of 5 minutes to 48 hours.

If it is desired to provide a composition with steviol glycosides in enriched or purified form, or where certain steviol glycosides are separated from one another, further purification can be carried out. Such enrichment or purification of steviol glycoside components can be carried out on the medium in which fermentation took place, or the medium can then be dried down prior to purification. For example, medium can be dried down using lyophilization to form a dry composition (e.g., powder or flakes) including steviol glycosides that can be subsequently processed.

As used herein, the term "total steviol glycosides" (TSG) is calculated as the sum of the content of all steviol glycosides in a composition on a dry (anhydrous) basis.

In some modes of practice, dried fermentation broth enriched for steviol glyosides is used as the starting material for purification. For example, a solvent or solvent combination can be added to the dried fermentation broth to dissolve or suspend material that includes the steviol glycosides. An exemplary combination for dissolving the steviol glycosides is a mixture of water and an alcohol (e.g., 50:50 ethanol:water). To facilitate dissolving or suspending, the dried broth materials can be heated at a temperature above room temperature, such as in the range of 40° C.-60° C. Mechanical disruption of the dried broth materials can also be performed, such as by sonication. The dissolved or suspended broth materials can be filtered using a micron or sub-micron prior to further purification, such as by preparative chromatography.

Dried fermentation broth enriched for steviol glycoside compounds can be subjected to purification, such as by reverse phase liquid chromatography. A suitable resin can be used to retain steviol glycoside compounds in the column, with removal of hydrophilic compounds which get washed through the column with a liquid such as water. Elution of steviol glycosides from the column can be accomplished a suitable solvent or solvent combination such as acetonitrile or methanol.

Elution of steviol glycosides from a reverse phase column can yield a composition which can be useful for any one of a variety of purposes. For example, a purified steviol glycoside composition can be used as a sweetener composition for oral ingestion or oral use. The composition can be defined with regards to the steviol glycosides in the composition.

Steviol glycoside-producing *S. cerevisiae* strains were constructed using methods as described in WO 2011/153378, WO 2013/022989, WO 2014/122227, and WO 2014/122328, each of which is incorporated by reference in their entirety. The following sequences were used for construction of a parent strain (EFSC 3841): a recombinant gene encoding a *Synechococcus* sp GGPPS polypeptide (SEQ ID NO:1), a recombinant gene encoding a truncated *Zea mays* CDPS polypeptide (SEQ ID NO:2), a recombinant gene encoding an *A. thaliana* KS polypeptide (SEQ ID NO:3), a recombinant gene encoding a recombinant *S. rebaudiana* KO polypeptide (SEQ ID NO:4, SEQ ID NO:5), a recombinant gene encoding an *A. thaliana* ATR2 polypeptide (SEQ ID NO:6, SEQ ID NO:7), a recombinant gene encoding an *O. sativa* EUGT 11 polypeptide (SEQ ID NO:8), a recombinant gene encoding an SrKAHe1 polypeptide (SEQ ID NO:9, SEQ ID NO:10), a recombinant gene encoding an *S. rebaudiana* CPR8 polypeptide (SEQ ID NO:11, SEQ ID NO:12), a recombinant gene encoding an *S. rebaudiana* UGT85C2 polypeptide (SEQ ID NO:13), a recombinant gene encoding an *S. rebaudiana* UGT74G1 polypeptide (SEQ ID NO:14), a recombinant gene encoding an *S. rebaudiana* UGT76G1 polypeptide (SEQ ID NO:15), and a recombinant gene encoding an *S. rebaudiana* UGT91D2 variant (or functional homolog), UGT91D2e-b, (SEQ ID NO:16) polypeptide produced steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. (Additional variants, except T144S, M152L, L213F, S364P, and G384C variants, described in Table 12 and Example 11 of PCT/US2012/050021 could be used.) GeneArt codon-optimized sequence encoding a *S. rebaudiana* UGT91D2e-b with the amino acid modifications L211M and V286A (SEQ ID NO:16 for amino acid sequence; codon optimized nucleotide sequence is set forth in SEQ ID NO:17).

Strain EFSC 4240 is derived from the parent strain described above and additionally includes a codon-optimized CPR1 from *S. rebaudiana* (SEQ ID NO:18 corresponding to amino acid SEQ ID NO:19).

In some embodiments, suitable methods of the present disclosure are illustrated and exemplified in the various embodiments set out below:

The present invention generally relates to methods for producing steviol glycosides using engineered yeast, as well as fermentation compositions, and fermentation products that include one or more steviol glycosides. Fermentation conditions of the disclosure can promote one or more of the following: increased steviol glycoside titers from the engineered yeast, increased cell activity including increased steviol glycoside production rates, reduced fermentation times, and reduced biomass concentrations. In exemplary embodiments the methods can be used for the production of steviol glycosides such as rebaudioside M, rebaudioside D, rebaudioside A, rebaudioside B, etc.

One embodiment of the invention provides a method for producing steviol glycoside(s), which includes at least steps (a) and (b) that involve the growth and fermentation of engineered yeast. In step (a) (i.e., a first phase) engineered yeast capable of producing one or more steviol glycoside(s) are grown in a medium at one or more growth rate(s) (dilution rate(s)) within a first range. Also in step (a), a composition comprising glucose is added to the medium according to a first mode that causes the yeast to grow within the first range. In step (b) (i.e., a second phase) the engineered yeast are fermented to produce the one or more steviol glycoside(s) where a composition comprising glucose is added to the medium according to a second mode that is different than the first mode. During step b), adding according to the second mode causes the yeast grow at one or more growth rate(s) (dilution rate(s)) within a second range which is less than the first range.

In an exemplary method, the yeast have a growth rate in step (a) in the range of about 0.06 l/h to about 0.15 l/hr, and a growth rate in step (b) in the range of about 0.015 l/h to about 0.09 l/hr. The change in growth rate from step (a) to step (b) can be caused by a change in "mode" of addition, such as by changing the rate of addition of a glucose-containing composition to the media, or changing how the glucose-containing composition is added to the media, such as providing a non-constant rate of feeding in step (a) and then a constant rate of feeding in step (b).

In another exemplary method, the engineered yeast is grown to a biomass amount in the range of 5 g dcw/L to 60 g dcw/L in step (a) and then to a biomass amount that does not exceed 150 g dcw/L in step (b).

The invention also provides a fermentation medium comprising steviol glycoside(s) obtained according to the method of the disclosure, and also a steviol glycoside composition obtained from the fermentation medium.

Additional embodiments of the invention numbered and set out below include:

1. A method for producing steviol glycoside(s), the method comprising steps of:
   (a) growing engineered yeast capable of producing one or more steviol glycoside(s) in a medium, wherein the engineered yeast grown at one or more growth rate(s) (dilution rate(s)) within a first range; and wherein a composition comprising glucose is added to the medium according to a first mode;
   (b) fermenting the engineered yeast to produce the one or more steviol glycoside(s), wherein during fermenting a composition comprising glucose is added to the medium according to a second mode that is different than the first mode, and during fermenting the yeast grow at one or more growth rate(s) (dilution rate(s)) within a second range, wherein the second range is less than the first range.

2. The method of embodiment 1 where in step (a) the growth rate (dilution rate) is 0.06 l/h or greater.

3. The method of embodiment 2 where in step (a) the first range is 0.06 l/h to 0.17 l/hr.

4. The method of embodiment 3 where in step (a) the first range is 0.09 l/h to 0.15 l/hr.

5. The method of embodiment 1 where in step (b) the growth rate (dilution rate) is 0.09 l/h or less.

6. The method of embodiment 5 where in step (b) the second range is 0.015 l/h to 0.09 l/hr.

7. The method of embodiment 6 where in step (b) the second range is 0.015 l/h to 0.06 l/hr.

8. The method of embodiment 1 wherein the growth rate (dilution rate) in step (b) is in the range of 50-100% of a maximum growth rate (dilution rate) in step (a).

9. The method of embodiment 1 where in step (a) the composition comprising glucose is added to the medium according to the first mode which is a non-constant rate of feeding.

10. The method of embodiment 1 where in step (b) the composition comprising glucose is added to the medium according to the second mode which is a constant rate of feeding.

11. The method of embodiment 10 wherein the constant rate of feeding is not greater than 10 g glucose/L media/h.

12. The method of embodiment 11 wherein the constant rate of feeding is in the range of 2 g glucose/L media/h to 10 g glucose/L media/h.

13. The method of embodiment 1 where in step (a) comprises one or more substeps of changing the first mode of adding glucose to reduce the growth rate of the engineered yeast.

14. The method of embodiment 1 where in step (b) a base is added to provide the medium with a pH that is higher than the pH of the medium in step (a).

15. The method of embodiment 14 where in step (b) the pH of the medium is 6.0 or greater.

16. The method of embodiment 1 where step (a) is started at a time when there is less than 3 g/L of glucose in the medium.

17. The method of embodiment 16 where step (a) is performed up to a time of 40 hours from the start of step (a) time.

18. The method of embodiment 16 where step (b) is performed at a time of 30 hours or later from the start of step (a).

19. The method of embodiment 1 where step (b) is performed up to 130 hours from an initial culturing of the engineered yeast.

20. The method of embodiment 1 where in step (a) the engineered yeast are grown to a biomass amount of at least 5 g dcw/L.

21. The method of embodiment 20 where in step (a) the engineered yeast are grown to a biomass amount in the range of 20 g dcw/L to 60 g dcw/L.

22. The method of embodiment 1 where in step (b) the engineered yeast do not grow to a biomass amount of greater than 180 g dcw/L.

23. The method of any of the previous embodiments further comprising a step of providing a seed medium comprising the engineered yeast, wherein the seed medium is used to form the first medium of step (a).

24. The method of any of the previous embodiments where, in step (b), the second medium comprises glucose, a nitrogen source, a potassium source, a magnesium source, a phosphate source, a magnesium source, trace metals, vitamins, and an antifoam agent.

25. The method of any of the previous embodiments wherein the one or more steviol glycoside(s) comprise rebaudioside M, rebaudioside D, or both rebaudioside M and rebaudioside D.

26. The method of any of the previous embodiments wherein the engineered yeast is selected from the group consisting of species of *Candida*, *Kloeckera* (*Hanseniaspora*), *Kluyveromyces*, *Lipomyces*, *Pichia* (*Hansenula*), *Rhodotorula*, *Saccharomycete*, *Saccharomyces*, *Schizosaccharomyces*, *Torulopsis*, *Torulaspora*, *Yarrowia*, and *Zygosaccharomyces*.

27. The method of embodiment 26 wherein the engineered yeast is *Saccharomyces cerevisiae*.

28. The method of any of the previous embodiments wherein the engineered yeast expresses one or more exogenous nucleic acid(s) encoding one or more of the following proteins heterologous to the yeast: GGPPS polypeptide, an ent-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91 D2 polypeptide, and a EUGT11 polypeptide 29. The method of any of the previous embodiments wherein the engineered yeast expresses one or more exogenous nucleic acid(s) encoding one or more of the following proteins heterologous to the yeast: a GGPPS polypeptide, a truncated *Zea mays* CDPS polypeptide, an *A. thaliana* KS polypeptide a *S. rebaudiana* KO polypeptide, an *A. thaliana* ATR2 polypeptide, an *O. sativa* EUGT 11 polypeptide, a SrKAHe1 polypeptide, a *S. rebaudiana* CPR8 polypeptide, an *S. rebaudiana* UGT85C2 polypeptide, an *S. rebaudiana* UGT74G1 polypeptide, a *S. rebaudiana* UGT76G1 polypeptide, a *S. rebaudiana* UGT91D2 variant or functional homolog, and a UGT91D2e-b polypeptide.

30. A fermentation medium comprising steviol glycoside obtained according to the method of any of the previous embodiments.

31. A steviol glycoside composition obtained according to the method of any of embodiments 1-29.

32. The method of embodiment 1 where during step (a) the concentration of glucose is not greater than 5 g/L in the medium.

33. The method of embodiment 32 where during step (a) the concentration of glucose is not greater than 5 g/L in the medium.

34. The method of embodiment 1 where during step (b) the concentration of glucose is not greater than 5 g/L in the medium.

35. The method of embodiment 34 where during step (b) the concentration of glucose is not greater than 5 g/L in the medium.

Disclosed is also a method of producing steviol glycosides using simultaneous saccharification and fermentation (SSF) to limit glucose release and keep glucose levels below those that stimulate fermentation in yeast such as the genera *Saccharomyces*. This approach typically uses sugars in polymeric form (e.g. starch, dextrins, cellulose, xylan) as the fermentation substrate. In some embodiments, the carbon source is a polysaccharide (e.g. greater than 10 monomers, an oligosaccharide (e.g. less than 10 monomers) or combinations thereof.

Since yeast typically does not efficiently consume polymeric sugars, an enzyme may be added to break the polymer into glucose monomers. As the name SSF suggests, the breakdown of sugars into monomers, saccharification, and the fermentation of the monomers occurs at the same time and typically in the same reaction vessel.

In one embodiment, SSF may use starch and glucoamylase (EC 3.2.1.3). In other embodiments, cellulosic hydrolysate and cellulase are used. Other embodiments include isomaltose, maltose, panose, maltotriose.

The examples show using maltodextrin (glucose chains of 4-7 glucose molecules, Sigma 419699) and alpha-amylase (product number and EC number 3.2.1.1) to create an SSF system. This approach, although common in industrial ethanol production, is not typically used in the production of yeast cell mass and biomass derived products. Furthermore, the dosing of enzyme required in yeast capable of producing ethanol is significantly different in yeast capable of producing steviol glycosides such as Reb D and Reb M. This process may carried out through the addition of enzymes or by engineering the glucoamylase into the yeast capable of producing steviol glycosides. In some embodiments, cellulosic hydrolysate and cellulase may be provided.

Saccharification enzymes are reviewed in Lynd, L. R., et al. (Microbiol. Mol. Biol. Rev., 66:506-577, 2002). At least one enzyme may be used, and typically a saccharification enzyme consortium may be used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group In some embodiments, the disclosed SSF may produce substantially no ethanol during a particular growing time period. In other embodiments, the disclosed SSF may produce substantially no ethanol during the entire growing time period. In other embodiments, the ethanol produced by the SSF process is less than 10 g/L of ethanol during a particular growing time period. In other embodiments, the ethanol produced by the SSF process is less than 10 g/L of ethanol at any point in the growing time period.

Also disclosed is a method of producing steviol glycosides using non-fermentative carbons sources (namely, non-glucose carbon sources). Non-fermentative carbon sources are sources that do not trigger or reduces the Crabtree effect. For example, if the yeast is grown in higher glucose concentrations, the yeast can switch from aerobic metabolic pathways to ethanol producing anaerobic metabolism, even under highly aerated conditions. This shift, when propagating yeast is generally not desirable if the purpose is to generate substantial numbers of yeast cells for the production of a desired product. Even under highly aerated conditions, if the glucose concentration in a propagation medium exceeds, for example about 5 g/L, the yeast, e.g. *S. cerevisiae*, can sometimes begin to make ethanol (fermentative pathway). This is known as the "Crabtree" effect (suppression of respiration by high glucose). When not enough oxygen is present, metabolism may also shift to the fermentative pathway.

To help avoid or reduce the Crabtree effect, yeast (e.g. *Saccharomyces cerevisiae*) is often grown by yeast suppliers in well aerated yeast propagation tanks with tightly monitored glucose feed (typically molasses feedstock is used in a fed-batch process) to help ensure that glucose levels remain low enough that metabolism remains aerobic.

Exemplary non-fermentative carbon sources include trehalose, maltose, galactose, mannose, glycerol, and raffinose and combinations thereof. In some embodiments, growth on non-fermentative carbon sources increases the release extracellularly of the steviol glycosides. In other embodiments, growth on trehalose carbon sources increases the release extracellularly of the steviol glycosides.

Example 1

Production of Reb D and Reb M in a Two-Phase Feeding Process

For inoculum preparation, the yeast strain EFSC4240 was cultured in 150 mls of seed flask medium in 1 liter shake flasks at 250 rpm and 30° C. for 20-24 hours.

TABLE 1

| Seed Flask Medium | | | |
|---|---|---|---|
| Component | Formula | Concentration | Units |
| Biospringer 0251 yeast extract | | 7.5 | g/L |
| Glucose monohydrate | $C_6H_{12}O_6*H_2O$ | 22.0 | g/L |

For the fermentation, 75 mls of seed culture was transferred into initial fermentation medium, as in Table 2, with an initial volume of 0.75 liters (38.5% of tank level). Fed batch fermentations were carried out in 2 L New Brunswick BioFlo310 fermentors. Fermentation was controlled at pH 5.0 with 12% $NH_4OH$ and temperature was maintained at 30° C. throughout. The air flow rate was 1.75 SLPM and agitation rate was 1200 rpm throughout the fermentation.

Glucose concentration was kept limiting by controlling flow rates of fermentation feed medium. A 2-phase feeding strategy involved an initial exponential phase (feed phase I) beginning at 12 hours with a growth rate of u=0.12 l/h or higher while the feed phase H started in the range of 35-39 hours with constant flow rates. The phase H feeding involved constant feeding in the range of 14.4 to 22.96 g glucose/L broth/h. Feeding was continued until 1.0 liter of fermentation feed medium was delivered. Antifoam, Ivanhoe 1163B, was added to the feed medium at 1.3 g/L and additional bolus additions of 5 wt % antifoam solution were added as needed.

The medium was based on Verduyn et al (Verduyn C, Postma E, Scheffers W A, and Van Dijken J R Yeast. 1992 July; 8(7):501-17) with modifications as described in tables 2 and 3.

TABLE 2

| Component | Formula | Concentration | Units |
|---|---|---|---|
| Initial Fermentation Medium | | | |
| Glucose monohydrate | $C_6H_{12}O_6*H_2O$ | 22.0 | g/L |
| Ammonium sulfate | $(NH_4)_2SO_4$ | 5.0 | g/L |
| Monobasic potassium phosphate | $KH_2PO_4$ | 3.0 | g/L |
| Magnesium sulfate heptahydrate | $MgSO_4*7\,H_2O$ | 0.5 | g/L |
| Trace metals stock | | 10.0 | ml/L |
| Vitamin stock | | 12.0 | ml/L |
| Trace Metals Stock Solution | | | |
| Disodium edetate | $C_{10}H_{14}N_2Na_2O_8*2H_2O$ | 15 | g/L |
| Zinc sulfate heptahydrate | $ZnSO_4*7H_2O$ | 4.5 | g/L |
| Manganese (II) chloride tetrahydrate | $MnCl_2*4H_2O$ | 1.026 | g/L |
| Cobalt (II) chloride hexahydrate | $CoCl_2*6H_2O$ | 0.32 | g/L |
| Copper (II) sulfate heptahydrate | $CuSO_4*5H_2O$ | 0.3 | g/L |
| Sodium molybdate dihydrate | $Na_2MoO_4*2H_2O$ | 0.4 | g/L |

TABLE 2-continued

| Component | Formula | Concentration | Units |
|---|---|---|---|
| Calcium chloride dihydrate | $CaCl_2 * 2H_2O$ | 3 | g/L |
| Iron (II) sulfate heptahydrate | $FeSO_4 * 7H_2O$ | 3 | g/L |
| Boric acid | $H_3BO_3$ | 1 | g/L |
| Potassium iodide | KI | 0.1 | g/L |
| Vitamin Stock Solution | | | |
| d-Biotin | $C_{10}H_{16}N_2O_3S$ | 50 | mg/L |
| Calcium pantothenate | $C_{18}H_{32}CaN_2O_{10}$ | 1000 | mg/L |
| Nicotinic acid | $C_6H_5NO_2$ | 1000 | mg/L |
| Thiamine hydrochloride | $C_{12}H_{17}ClN_4OS \cdot HCl$ | 1000 | mg/L |
| Pyridoxine hydrochloride | $C_8H_{11}NO_3 \cdot HCl$ | 1000 | mg/L |
| p-aminobenzoic acid | $C_7H_7NO_2$ | 200 | mg/L |
| myo-inositol | $C_6H_{12}O_6$ | 25000 | mg/L |

TABLE 3

Fermentation Feed Medium

| Component | Formula | Concentration | Units |
|---|---|---|---|
| Glucose monohydrate | $C_5H_{12}O_6 * H_2O$ | 660 | g/L |
| Antifoam | | 1.3 | g/L |
| Potassium sulfate | $K_2SO_4$ | 4.2 | g/L |
| Sodium sulfate | $Na_2SO_4$ | 0.336 | g/L |
| Magnesium sulfate heptahydrate | $MgSO_4 * 7H_2O$ | 6.12 | g/L |
| Monobasic potassium phosphate | $KH_2PO_4$ | 10.8 | g/L |
| Trace metal stock | | 14.4 | mL/L |
| Vitamin stock | | 14.4 | mL/L |

TABLE 4

Increased glucose medium feed rates in both phases of the 2 phase feeding regime

| Phase I feed rate (mu in 1/h) | Phase II feed rate g dx/L/h | Reb D conc g/L | Reb M conc g/L | RebDM conc g/L | RebDM Rate mg/L/h | Fermentation Time hours | Biomass conc g/L |
|---|---|---|---|---|---|---|---|
| 0.12 | 14.4 | 1.08 | 1.89 | 2.97 | 25.2 | 117.9 | 114.4 |
| 0.15 | 19.7 | 0.85 | 1.67 | 2.52 | 27.8 | 90.75 | 111.4 |
| 0.18 | 23.0 | 0.49 | 0.99 | 1.48 | 19.5 | 75.8 | 90.3 |

Example 2

Production of Reb D and Reb M Using Different Carbon Sources

A base media composition was prepared using the recipe in Table 5. The base media was used to further prepare a maltose-only media, trehalose-only media, glucose-only media, galactose-only media, mannose-only media, glycerol-only media, and raffinose-only media. The concentration for each sugar substrate was 100 g/L. Each media was adjusted to pH 5.6 and filter sterilized through 0.2 urn filter. 20 ml media per 250 ml flask was used. The pH was adjusted using either KOH or H2SO4.

TABLE 5

Base media composition for seed and production flasks

| Component | Conc. [g/L] |
|---|---|
| NH4SO4 | 5.0 |
| Urea | 30 |
| KH2PO4 | 15 |
| MgSO4*7 H2O | 2.5 |
| Trace metal stock | 10 |
| Vitamin stock | 12 |
| MES* | 38.2 |
| De-ionized water | adjust to 1 L after addition of carbon source |

*MES = 2-(N-morpholino)ethanesulfonic acid

TABLE 5-continued

| Component | Formula | Concentration | Units |
|---|---|---|---|
| Trace Metals Stock Solution | | | |
| Disodium edetate | $C_{10}H_{14}N_2Na_2O_8*2H_2O$ | 15 | g/L |
| Zinc sulfate heptahydrate | $ZnSO_4*7H_2O$ | 4.5 | g/L |
| Manganese (II) chloride tetrahydrate | $MnCl_2*4H_2O$ | 1.026 | g/L |
| Cobalt (II) chloride hexahydrate | $CoCl_2*6H_2O$ | 0.32 | g/L |
| Copper (II) sulfate heptahydrate | $CuSO_4*5H_2O$ | 0.3 | g/L |
| Sodium molybdate dihydrate | $Na_2MoO_4*2H_2O$ | 0.4 | g/L |
| Calcium chloride dihydrate | $CaCl_2*2H_2O$ | 3 | g/L |
| Iron (II) sulfate heptahydrate | $FeSO_4*7H_2O$ | 3 | g/L |
| Boric acid | $H_3BO_3$ | 1 | g/L |
| Potassium iodide | KI | 0.1 | g/L |
| Vitamin Stock Solution | | | |
| d-Biotin | $C_{10}H_{16}N_2O_3S$ | 50 | mg/L |
| Calcium pantothenate | $C_{18}H_{32}CaN_2O_{10}$ | 1000 | mg/L |
| Nicotinic acid | $C_6H_5NO_2$ | 1000 | mg/L |
| Thiamine hydrochloride | $C_{12}H_{17}ClN_4OS \cdot HCl$ | 1000 | mg/L |
| Pyridoxine hydrochloride | $C_8H_{11}NO_3 \cdot HCl$ | 1000 | mg/L |
| p-aminobenzoic acid | $C_7H_7NO_2$ | 200 | mg/L |
| myo-inositol | $C_6H_{12}O_6$ | 25000 | mg/L |

TABLE 6

Carbon sources for Production flasks (100 g/L each)

Trehalose
Maltose
Galactose
Mannose
Glycerol
Raffinose
Glucose

The yeast culture (4240), as used in Example 1, was started from a glycerol stock culture (20% v/v glycerol). The stock was used to inoculate a flask containing the glucose-only media described above. Incubation occurred at 30° C., 250 rpm, with 50 ml of media in a 250 ml flask. After 24 hours, this seed flask had reached 2 g/l cell density and had residual glucose remaining. This culture was spun in the centrifuge (4000 rpm for 5 min) to pellet the cells. The broth was decanted and the cells were washed one time with sterile Butterfields Phosphate Buffer (pH 7.2) and the centrifugation and decanting repeated to remove residual glucose. Cells were suspended to a cell density of 4 g/l in sterile Butterfields phosphate buffer (pH 7.2). 1 ml of this cell suspension was used to inoculate production flasks (5% inocula).

Production flasks were incubated at 30° C., 250 rpm in a shaker humidified to 80%. Flasks were harvested for Reb D and Reb M analysis when at least OD600 (Genesys 20 spec) of 10 had been reached in the culture. Using a known OD to cell dry weight conversion factor determined for this specification, this equates to approximately 7.5 g/l cells. If this OD was not reached in 120 hours, the flask was stopped at 120 hours and analysis performed at that time.

TABLE 7

Reb D and Reb M and Cell production on Various Carbon Sources

| | Normalized RebD & RebM production at harvest | Normalized rate (g/l/h) | Normalized specific rate (rate per 1 OD unit) | Cells (g/l) at harvest (OD/1.3) | Time of harvest (h) |
|---|---|---|---|---|---|
| Glucose | 1.0 | 1.0 | 1.0 | 8.5 | 30 |
| Mannose | 5.4 | 3.0 | 5.0 | 9.2 | 55 |
| Raffinose | 8.1 | 4.4 | 7.2 | 9.5 | 55 |
| Maltose | 3.3 | 1.8 | 2.5 | 11.2 | 55 |
| Galactose | 4.3 | 1.1 | 3.6 | 10.3 | 120 |
| Trehalose | 2.1 | 0.5 | 9.6 | 1.8 | 120 |
| Glycerol | 1.4 | 0.4 | 6.8 | 1.8 | 120 |

Table 7 shows normalized Reb D and Reb M production and rates. Normalized production is calculated by dividing the Reb D and Reb M in the experimental condition by the 100 g/l glucose condition.

These data show that the glucose-limited media containing ethanol-limiting substrates (i.e., mannose, raffinose, maltose, galactose, trehalose, or glycerol in these examples) perform better than glucose in Reb D and Reb M production. Volumetric Production was the highest on mannose, raffinose, galactose and trehalose. Specific production was the highest on mannose, raffinose, trehalose and glycerol. Mannose, raffinose, and trehalose were particularly impressive, with specific production rates of 5, 7.2, and 9.6 times (respectively) that of glucose.

Example 3

Production of Reb D and Reb M Using Different Carbon Sources

As in the prior example, a base medium composition was prepared using the recipe in Table 5. This base medium was used to further prepare a glucose-only medium, a maltose-only medium, a fructose-only medium, a raffinose-only medium, a galactose-only medium, and a mannose-only medium. The concentration for each sugar substrate was 100 g/L. Each medium was adjusted to pH 5.6 and filter sterilized through 0.2 urn filter. 20 ml media per 250 ml flask was used. The pH was adjusted using either KOH or H2SO₄.

A yeast culture of a different steviol-producing *Saccharomyces cerevisiae* (4466) was started from a glycerol stock culture (20% v/v glycerol). The stock was used to inoculate a flask containing the glucose-only media described above. Incubation occurred at 30° C., 250 rpm, with 50 ml of media in a 250 ml flask. After 24 hours, this seed flask had reached 1 g/l cell density and had residual glucose remaining. This culture was spun in the centrifuge (4000 rpm for 5 min) to pellet the cells. The broth was decanted and the cells were washed one time with sterile Butterfields Phosphate Buffer (pH 7.2) and the centrifugation and decanting repeated to remove residual glucose. Cells were suspended to a cell density of 4 g/l in sterile Butterfields phosphate buffer (pH 7.2). 0.5 ml of this cell suspension was used to inoculate production flasks (2.5% inocula).

Production flasks were incubated at 30° C., 250 rpm in a shaker humidified to 80%. Flasks were harvested for Reb D and Reb M at 118 hours. OD600 was also measured at 118 h (Genesys 20 spec). Using a known OD to cell dry weight conversion factor each OD unit translates to 0.75 g/l cells.

Reb D and Reb M analysis was performed on whole cell broth, cell free supernatant and washed cells. For cell-free samples, 100 uL of whole broth was mixed with 1.4 ml purified water, and centrifuged at 10,000 rpm in a microcentrifuge for 3 min. This washing was repeated 3 times before analysis. The resultant washed cells were used for the washed cell analysis. Supernatant from the first spin was used for analysis of the cell-free supernatant, which is listed below as the extracellular analysis.

Table 3-1 shows the content of RebD, RebM, and the sum of RebD and Reb M ("RebD+M below), in g/L, in the whole broth, the extracellular cell-free supernatant, and the washed cell pellet. This data is an average of replicate flasks for each condition. % Extracellular is calculated by dividing the g/l extracellular by the g/l whole broth. Table 3-2 shows normalized RebD and RebM production in terms of mg/L/hour and Table 3-3 shows normalized RebD and RebM production in terms of mg/g/hour.

TABLE 3-1

RebDM Production on Various Carbon Sources, Intracellular, Extracellular and Whole Broth at 118 h

| | g/L Whole Broth | | | g/L Extracellular | | | g/L Washed Pellet | | | % Extracellular | | |
|---|---|---|---|---|---|---|---|---|---|---|---|---|
| | RebD | RebM | RebD + M | RebD | RebM | RebD + M | RebD | RebM | RebD + M | RebD | RebM | RebD + M |
| Glucose | 0.008 | 0.037 | 0.045 | 0.003 | 0.018 | 0.021 | 0.005 | 0.020 | 0.024 | 39.4% | 48.5% | 46.9% |
| Maltose | 0.010 | 0.042 | 0.052 | 0.006 | 0.022 | 0.028 | 0.004 | 0.020 | 0.024 | 61.8% | 52.8% | 54.5% |
| Fructose | 0.009 | 0.040 | 0.049 | 0.006 | 0.019 | 0.025 | 0.003 | 0.021 | 0.024 | 70.9% | 46.6% | 51.1% |
| Raffinose | 0.092 | 0.394 | 0.485 | 0.062 | 0.236 | 0.298 | 0.030 | 0.158 | 0.188 | 67.5% | 59.9% | 61.3% |
| Galactose | 0.014 | 0.065 | 0.079 | 0.007 | 0.031 | 0.037 | 0.007 | 0.034 | 0.041 | 47.1% | 47.7% | 47.6% |
| Mannose | 0.022 | 0.092 | 0.113 | 0.015 | 0.058 | 0.072 | 0.007 | 0.034 | 0.041 | 68.6% | 62.8% | 63.9% |

TABLE 3-2

RebDM Productivity on Various Carbon Sources, Intracellular, Extracellular and Whole Broth at 118 h

| | mg/L/h Whole Broth | | | mg/L/h Extracellular | | | mg/L/h Washed Pellet | | |
|---|---|---|---|---|---|---|---|---|---|
| | RebD | RebM | RebD + M | RebD | RebM | RebD + M | RebD | RebM | RebD + M |
| Glucose | 0.068 | 0.314 | 0.381 | 0.027 | 0.152 | 0.179 | 0.041 | 0.165 | 0.206 |
| Maltose | 0.086 | 0.354 | 0.441 | 0.053 | 0.187 | 0.240 | 0.033 | 0.167 | 0.200 |
| Fructose | 0.076 | 0.336 | 0.412 | 0.054 | 0.157 | 0.211 | 0.022 | 0.180 | 0.202 |
| Raffinose | 0.776 | 3.338 | 4.114 | 0.524 | 1.998 | 2.522 | 0.252 | 1.339 | 1.592 |
| Galactose | 0.117 | 0.550 | 0.667 | 0.055 | 0.262 | 0.317 | 0.062 | 0.288 | 0.350 |
| Mannose | 0.183 | 0.776 | 0.960 | 0.126 | 0.487 | 0.613 | 0.058 | 0.289 | 0.347 |

TABLE 3-3

RebDM Specific Productivity on Various Carbon Sources, Intracellular, Extracellular and Whole Broth at 118 h

| | mg/g/h Whole Broth | | | mg/g/h Extracellular | | | mg/g/h Washed Pellet | | |
|---|---|---|---|---|---|---|---|---|---|
| | RebD | RebM | RebD + M | RebD | RebM | RebD + M | RebD | RebM | RebD + M |
| Glucose | 0.003 | 0.016 | 0.019 | 0.001 | 0.008 | 0.009 | 0.002 | 0.008 | 0.010 |
| Maltose | 0.008 | 0.032 | 0.040 | 0.005 | 0.017 | 0.022 | 0.003 | 0.015 | 0.018 |
| Fructose | 0.006 | 0.026 | 0.032 | 0.004 | 0.012 | 0.016 | 0.002 | 0.014 | 0.016 |
| Raffinose | 0.033 | 0.140 | 0.172 | 0.022 | 0.084 | 0.106 | 0.011 | 0.056 | 0.067 |
| Galactose | 0.014 | 0.067 | 0.081 | 0.007 | 0.032 | 0.038 | 0.007 | 0.035 | 0.042 |
| Mannose | 0.014 | 0.059 | 0.073 | 0.010 | 0.037 | 0.046 | 0.004 | 0.022 | 0.026 |

Consistent with the results show in Table 7, total production of RebD and RebM was the highest on mannose, raffinose, and galactose. Raffinose was surprisingly productive, with total production of RebD and RebM more than 10 times that for glucose. This confirms, and even exceeds, the very high normalized production of 8.1 for raffinose shown in Table 7. Mannose was also impressive, with total production of RebD and RebM more than 2.5 times that for glucose.

The percentage of extracellular RebD and RebM increased significantly on the substrates maltose, raffinose and mannose; raffinose and mannose both had over 60% of the total RebD and RebM extracellularly. Commercially, it can be significantly easier to purify extracellular steviol glycosides rather than lysing cells and having to isolate the steviol glycosides from all of the other intracellular components. A commercial producer may elect to leave the intracellular steviol glycosides in the cell, selling the biomass as a feed component at a significantly lower margin. Hence, increasing the percentage of RebD plus RebM from 46.9% for glucose to 61.3% for raffinose and 63.9% for mannose increases the effective yield by over 30% (61.3/46.9) for raffinose and over 36% (63.9/46.9) for mannose. This, combined with the higher total production with raffinose and mannose, led to extracellular production of RebD+RebM for raffinose of 14 times that of glucose and for mannose of 3.4 times that of glucose.

Example 4

Production of Reb D and Reb M Using Simultaneous Saccharification and Fermentation Media was prepared using the recipe in Table 8 with trace elements and vitamins from Table 5. Maltodextrin required gentle heating of the media to obtain solubilization (60° C.). Media cooled to room temperature was adjusted to pH 5.6, vitamin and trace addition was performed after cooling of media and filter sterilized through 0.2 urn filter. 20 ml media per 250 ml flask was used. The pH was adjusted using either KOH or H2SO4.

The yeast culture (4240) yeast was started from a glycerol stock culture (20% v/v glycerol). The stock was used to inoculate a flask containing the media described in Table 5 containing 20 g/L dextrose. Incubation occurred at 30° C., 250 rpm, with 20 ml of media in a 250 ml flask. After 24 hours, this seed flask had reached 2 g/l cell density and had residual glucose remaining. 1 ml of this cell suspension was used to inoculation production flasks (5% inocula). Immediately prior to inoculation alpha-amylase was added to the media at doses detailed in Table 9.

Flasks with the inoculum were incubated at 30° C., 250 rpm in a shaker humidified to 80%. Flasks with the culture were harvested for Reb D and Reb M analysis at 120 hours.

Normalized production is calculated by dividing the Reb D and Reb M in the experimental sample by the no-enzyme-added sample with 200 g/l dextrose (g equivalent sugar). These data show 6-13× higher production of Reb D and Reb M using a SSF process compared to using only glucose.

TABLE 8

Media Composition for Seed and Production Flasks SSF

| Component | Conc. [g/L] |
| --- | --- |
| NH4SO4 | 5.0 |
| Urea | 30 |
| KH2PO4 | 15 |

TABLE 8-continued

Media Composition for Seed and Production Flasks SSF

| Component | Conc. [g/L] |
| --- | --- |
| MgSO4*7H2O | 2.5 |
| Glucose monohydrate | 11 |
| Trace metal stock | 10 |
| Vitamin stock | 12 |
| Maltodextrin | 200 g/l |
| MES* | 38.2 |
| Deionized Water | To 1 L final volume |

*MES = 2-(N-morpholino)ethanesulfonic acid

TABLE 9

Normalized of Reb D and Reb M production vs. Enzyme Dosing

| % volume alpha-amylase added per total flask volume | Normalized RebD & RebM |
| --- | --- |
| 200 g/l glucose control, 0% enzyme | 1.00 |
| 0.0000% | 1.19 |
| 0.0010% | 6.27 |
| 0.0015% | 6.37 |
| 0.0020% | 7.94 |
| 0.0025% | 9.45 |
| 0.0025% | 8.13 |
| 0.0030% | 8.80 |
| 0.0035% | 10.99 |
| 0.0040% | 11.86 |
| 0.0045% | 13.98 |
| 0.0050% | 12.57 |

Example 5

Medium: each shake flask contained 2% yeast extract and 2% carbon source, 1× trace mineral and 1× salts. The pH of the medium was adjusted to 5.1 with NaOH and autoclaved at 121° C. for 30 minutes.

Seed flask: 1 vial of glycerol stock was used to inoculate a 500 ml baffled shake flask containing 100 ml of glucose medium. The shake flask was grown at 30° C. for 24 hours with vigorous mixing (250 rpm). 10 ml seed culture was used to inoculate a 300 ml baffled shake flask containing 50 ml of base medium containing various carbohydrates.

The seed culture has the following profile before transferring to the production flasks: O.D. at 600 nm=27.2, 0 g/L glucose, 9 g/L ethanol, 2.4 g/L glycerol, and 0.25 g/L acetate.

Production flasks: Each condition was run in duplicates. The production flasks were incubated in a 30° C. shaking incubator set at 250 rpm. A 5 ml sample was taken after 24 hours, 46 hours, and 110 hours. The cell density was estimated by optical density at 600 nm after diluting the broth 1:200 with deionized water. The broth was filtered through a 0.45 urn filter and used for HPLC analysis. Total steviol glycoside was determined after mixing broth with an equal amount of 80% v/v DMSO and heat at 80° C. for 30 minutes in a sealed glass vial. The cell debris was filtered off using a 0.45 urn filter before HPLC analysis. The octopus UPLC method was used to measure total or extracellular steviol glycoside concentrations.

The cells grew well in glucose and fructose medium, but poorly in glycerol and trehalose medium. At the end of 110 hours, cells completely consumed trehalose but not glycerol. Since there was a significant amount of evaporation, it is not clear how much glycerol was used. The optical density of the shake flask reached about 65-70 nm within 24 hours for glucose and fructose treatments. Subsequent increase in O.D. was most likely due to evaporation. It is reasonable to assume that trehalose treatments also reached a similar O.D. at the end. There was no measurable amount of ethanol in any of the flasks at any time points. The primary metabolites found were ~0.3 g/L succinate and ~0.2 g/L glycerol.

|  | O.D. 600 nm | | | pH | | |
| --- | --- | --- | --- | --- | --- | --- |
|  | T24 | T46 | T110 | T24 | T46 | T110 |
| glycerol-1 | 32.4 | 41 | 92 | 5.67 | 5.5 | 5.26 |
| glycerol-2 | 34.8 | 40.8 | 75.2 | 5.61 | 5.5 | 5.4 |
| fructose-1 | 66.8 | 80.2 | 120.4 | 4.73 | 4.6 | 4.59 |
| fructose-2 | 69.2 | 74.8 | 118.6 | 4.76 | 4.8 | 4.7 |

-continued

|  | O.D. 600 nm | | | pH | | |
| --- | --- | --- | --- | --- | --- | --- |
|  | T24 | T46 | T110 | T24 | T46 | T110 |
| glucose-1 | 68 | 75.6 | 126.8 | 4.63 | 4.6 | 4.55 |
| glucose-2 | 64.4 | 76.6 | 135.4 | 4.58 | 4.5 | 4.48 |
| trehalose-1 | 31.8 | 38.8 | 169.4 | 5.53 | 5.2 | 4.83 |
| trehalose-2 | 30.2 | 35.6 | 115.8 | 5.46 | 5.1 | 4.86 |

The total concentrations of reb D, reb M, and reb A were determined for all three time points and the results are shown below. For glycerol and trehalose samples, there are similar concentrations of reb D and reb M and much lower concentrations of reb A in the broth. However, in the glucose and fructose samples, reb M concentration is the highest, followed by reb A, and then reb D.

| ppm | rebD | | | rebM | | | rebA | | |
| --- | --- | --- | --- | --- | --- | --- | --- | --- | --- |
|  | T24 | T46 | T110 | T24 | T46 | T110 | T24 | T46 | T110 |
| glycerol-1 | 5.43 | 11.81 | 39.11 | 8.88 | 9.57 | 39.33 | 3.45 | 3.54 | 6.04 |
| glycerol-2 | 7.6 | 14.78 | 32.69 | 9.21 | 9.55 | 28.22 | 3.11 | 3.34 | 4.54 |
| fructose-1 | 1.77 | 2.64 | 3.93 | 6.94 | 7.46 | 10.31 | 3.74 | 3.99 | 5.2 |
| fructose-2 | 2.24 | 2.57 | 3.67 | 7.93 | 7.66 | 10.64 | 4.02 | 3.89 | 5.05 |
| glucose-1 | 2.02 | 3.01 | 5.99 | 12.08 | 12.99 | 21.2 | 5.8 | 7.05 | 10.16 |
| glucose-2 | 1.22 | 3.16 | 5.85 | 9.65 | 11.68 | 20.89 | 3.97 | 6.11 | 10.43 |
| trehalose-1 | 5.15 | 19.48 | 202.11 | 11.21 | 34.2 | 208.03 | 3.07 | 4.83 | 52.44 |
| trehalose-2 | 5.49 | 20.29 | 119.18 | 10.75 | 33.5 | 122.24 | 3.18 | 4.35 | 33.14 |

Extracellular concentration of steviol glycosides was only determined in the last sample point and the ratios of extracellular and total steviol glycosides are listed below. It is interesting to note that trehalose treatments, i.e., those using a glucose-limited medium employing an ethanol-limiting substrate in accordance with a preferred aspect of the invention, showed the highest amount of excretion of steviol glycosides (~50%) as compared to other treatments (~20%).

| ppm | T110 | | | | | | | | |
| --- | --- | --- | --- | --- | --- | --- | --- | --- | --- |
|  | rebD-total | rebD-extra | % | rebM-total | rebM-extra | % | rebA-total | rebA-extra | % |
| glycerol-1 | 39.11 | 2.38 | 6.09 | 39.33 | 7 | 17.80 | 6.04 | 0.48 | 7.95 |
| glycerol-2 | 32.69 | 1.66 | 5.08 | 28.22 | 4.83 | 17.12 | 4.54 | 0.67 | 14.76 |
| fructose-1 | 3.93 | 0.95 | 24.17 | 10.31 | 2.97 | 28.81 | 5.2 | 1.02 | 19.62 |
| fructose-2 | 3.67 | 0.89 | 24.25 | 10.64 | 2.99 | 28.10 | 5.05 | 0.99 | 19.60 |
| glucose-1 | 5.99 | 0.91 | 15.19 | 21.2 | 3.99 | 18.82 | 10.16 | 1.48 | 14.57 |
| glucose-2 | 5.85 | 1.19 | 20.34 | 20.89 | 4.53 | 21.69 | 10.43 | 2.07 | 19.85 |
| trehalose-1 | 202.11 | 94.4 | 46.71 | 208.03 | 102.68 | 49.36 | 52.44 | 21.08 | 40.20 |
| trehalose-2 | 119.18 | 59.5 | 49.92 | 122.24 | 63.47 | 51.92 | 33.14 | 13.67 | 41.25 |

To account for variable levels of evaporation, the concentration of total steviol glycoside was normalized against cell density (O.D.) and shown in the table below. Glycerol and trehalose grown cells had much higher per cell productivity and the productivity continued to increase throughout the time course than those grown on glucose and fructose.

|  | ppm RebD/OD | | | ppm RebM/OD | | | ppm RebA/OD | | |
| --- | --- | --- | --- | --- | --- | --- | --- | --- | --- |
|  | T24 | T46 | T110 | T24 | T46 | T110 | T24 | T46 | T110 |
| glycerol-1 | 0.17 | 0.29 | 0.43 | 0.27 | 0.23 | 0.43 | 0.11 | 0.09 | 0.07 |
| glycerol-2 | 0.22 | 0.36 | 0.43 | 0.26 | 0.23 | 0.38 | 0.09 | 0.08 | 0.06 |
| fructose-1 | 0.03 | 0.03 | 0.03 | 0.10 | 0.09 | 0.09 | 0.06 | 0.05 | 0.04 |

-continued

| | ppm RebD/OD | | | ppm RebM/OD | | | ppm RebA/OD | | |
|---|---|---|---|---|---|---|---|---|---|
| | T24 | T46 | T110 | T24 | T46 | T110 | T24 | T46 | T110 |
| fructose-2 | 0.03 | 0.03 | 0.03 | 0.11 | 0.10 | 0.09 | 0.06 | 0.05 | 0.04 |
| glucose-1 | 0.03 | 0.04 | 0.05 | 0.18 | 0.17 | 0.17 | 0.09 | 0.09 | 0.08 |
| glucose-2 | 0.02 | 0.04 | 0.04 | 0.15 | 0.15 | 0.15 | 0.06 | 0.08 | 0.08 |
| trehalose-1 | 0.16 | 0.50 | 1.19 | 0.35 | 0.88 | 1.23 | 0.10 | 0.12 | 0.31 |
| trehalose-2 | 0.18 | 0.57 | 1.03 | 0.36 | 0.94 | 1.06 | 0.11 | 0.12 | 0.29 |

What is claimed is:

1. A method for producing steviol glycoside(s), comprising growing engineered yeast capable of producing one or more steviol glycoside(s) in a glucose-limited medium that contains carbohydrates, wherein:
   (a) less than 50% by weight (wt %) of the carbohydrates in the glucose-limited medium is glucose, fructose, or glucose and fructose; and
   (b) at least 50 wt % of the carbohydrates in the glucose-limited medium is an ethanol production-limiting substrate that is raffinose, mannose, trehalose, or combinations thereof;
   wherein the engineered yeast expresses exogenous nucleic acids encoding:
      (a) a geranylgeranyl diphosphate synthase (GGPPS) polypeptide;
      (b) an ent-copalyl diphosphate synthase (CDPS) polypeptide;
      (c) a kaurene oxidase (KO) polypeptide;
      (d) a kaurene synthase (KS) polypeptide;
      (e) a steviol synthase (KAH) polypeptide;
      (f) a cytochrome P450 reductase (CPR) polypeptide; and
      (g) one or more uridine diphosphate (UDP) glycosyltransferases (UGTs) polypeptide.

2. The method of claim 1, wherein the steviol glycoside(s) comprise rebaudioside M, rebaudioside D, or both rebaudioside M and rebaudioside D.

3. The method of claim 1, wherein the engineered yeast is *Candida, Kloeckera (Hanseniaspora), Kluyveromyces, Lipomyces, Pichia (Hansenula), Rhodotorula, Saccharomycete, Saccharomyces, Schizosaccharomyces, Torulopsis, Torulaspora, Yarrowia,* or *Zygosaccharomyces*.

4. The method of claim 1, wherein at least 50 wt % of the steviol glycoside(s) produced is released extracellularly.

5. The method of claim 1, wherein the steviol glycoside(s) comprise rebaudioside M, and rebaudioside D, and wherein at least 50 wt % of the one or more steviol glycoside(s) produced is released extracellularly.

6. The method of claim 1, wherein less than 20 wt % of the carbohydrates in the glucose-limited medium is glucose, fructose, or glucose and fructose.

7. The method of claim 1, wherein less than 10 wt % of the carbohydrates in the glucose-limited medium is glucose, fructose, or glucose and fructose.

8. The method of claim 1, wherein less than 5 wt % of the carbohydrates in the glucose-limited medium is glucose, fructose, or glucose and fructose.

9. The method of claim 1, wherein at least 60 wt % of the carbohydrates in the glucose-limited medium is the ethanol production-limiting substrate that is raffinose, mannose, trehalose, or combinations thereof.

10. The method of claim 1, wherein at least 70 wt % of the carbohydrates in the glucose-limited medium is the ethanol production-limiting substrate that is raffinose, mannose, trehalose, or combinations thereof.

11. The method of claim 1, wherein at least 80 wt % of the carbohydrates in the glucose-limited medium is the ethanol production-limiting substrate that is raffinose, mannose, trehalose, or combinations thereof.

12. The method of claim 1, wherein at least 90 wt % of the carbohydrates in the glucose-limited medium is the ethanol production-limiting substrate that is raffinose, mannose, trehalose, or combinations thereof.

13. The method of claim 1, wherein at least 95 wt % of the carbohydrates in the glucose-limited medium is the ethanol production-limiting substrate that is raffinose, mannose, trehalose, or combinations thereof.

14. The method of claim 1, wherein the ethanol production-limiting substrate is raffinose.

15. The method of claim 1, wherein the ethanol production-limiting substrate is mannose.

16. The method of claim 1, wherein the ethanol production-limiting substrate is trehalose.

* * * * *

SEQUENCE LISTING

<160> NUMBER OF SEQ ID NOS: 19

<210> SEQ ID NO 1
<211> LENGTH: 297
<212> TYPE: PRT
<213> ORGANISM: Synechococcus

<400> SEQUENCE: 1

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285
```

```
Ala Asp Phe Ile Thr Arg Arg Gln His
    290                 295
```

<210> SEQ ID NO 2
<211> LENGTH: 827
<212> TYPE: PRT
<213> ORGANISM: Zea Mays

<400> SEQUENCE: 2

```
Met Val Leu Ser Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
                100                 105                 110

Asp Thr Ala Trp Val Gly Leu Val Pro Arg Leu Asp Gly Gly Glu Gly
            115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
                180                 185                 190

Lys Leu Ala Thr Glu Asp Glu Glu Ser Met Pro Ile Gly Phe Glu Leu
            195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
                260                 265                 270

Leu Leu Lys Leu Gln Ser Ser Asp Gly Ser Phe Leu Phe Ser Pro Ala
            275                 280                 285

Ala Thr Ala Tyr Ala Leu Met Asn Thr Gly Asp Asp Arg Cys Phe Ser
    290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

Arg Leu Gly Ile Ser Arg Tyr Phe Gln Lys Glu Ile Glu Gln Cys Met
                340                 345                 350

Asp Tyr Val Asn Arg His Trp Thr Glu Asp Gly Ile Cys Trp Ala Arg
            355                 360                 365
```

Asn Ser Asp Val Lys Glu Val Asp Asp Thr Ala Met Ala Phe Arg Leu
        370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
        435                 440                 445

Arg Arg Lys Glu Ala Glu Gly Ala Leu Arg Asp Lys Trp Ile Ile Ser
450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
            515                 520                 525

Cys Gln Ala Leu His Gln Leu Glu Trp Gln Gly Leu Lys Arg Trp Tyr
530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ala Ser Val Tyr Glu Pro Cys Arg Ala
                565                 570                 575

Ala Glu Arg Leu Ala Trp Ala Arg Ala Ala Ile Leu Ala Asn Ala Val
            580                 585                 590

Ser Thr His Leu Arg Asn Ser Pro Ser Phe Arg Glu Arg Leu Glu His
            595                 600                 605

Ser Leu Arg Cys Arg Pro Ser Glu Glu Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Trp Ala Glu Trp Val
            660                 665                 670

Arg Glu Lys Ala Asp Ala Ala Asp Ser Val Cys Asn Gly Ser Ser Ala
                675                 680                 685

Val Glu Gln Glu Gly Ser Arg Met Val His Asp Lys Gln Thr Cys Leu
            690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
            755                 760                 765

Ile Arg Glu Phe Val Gln Tyr Leu Leu Arg Leu Gly Glu Lys Lys Thr
770                 775                 780

```
Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825

<210> SEQ ID NO 3
<211> LENGTH: 785
<212> TYPE: PRT
<213> ORGANISM: Arabidopsis thaliana

<400> SEQUENCE: 3

Met Ser Ile Asn Leu Arg Ser Gly Cys Ser Ser Pro Ile Ser Ala
1               5                   10                  15

Thr Leu Glu Arg Gly Leu Asp Ser Glu Val Gln Thr Arg Ala Asn Asn
                20                  25                  30

Val Ser Phe Glu Gln Thr Lys Glu Lys Ile Arg Lys Met Leu Glu Lys
            35                  40                  45

Val Glu Leu Ser Val Ser Ala Tyr Asp Thr Ser Trp Val Ala Met Val
50                  55                  60

Pro Ser Pro Ser Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
210                 215                 220

Lys Asn Gly Ser Leu Phe Asp Ser Pro Ala Thr Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335
```

```
Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750
```

Phe Tyr Arg Lys Asp Asp Gly Phe Thr Ser Asn Asp Leu Met Ser Leu
            755                 760                 765

Val Lys Ser Val Ile Tyr Glu Pro Val Ser Leu Gln Lys Glu Ser Leu
    770                 775                 780

Thr
785

<210> SEQ ID NO 4
<211> LENGTH: 1542
<212> TYPE: DNA
<213> ORGANISM: Stevia rebaudiana

<400> SEQUENCE: 4

```
atggatgctg tgacgggttt gttaactgtc ccagcaaccg ctataactat tggtggaact    60
gctgtagcat tggcggtagc gctaatcttt tggtacctga atcctacac atcagctaga    120
agatcccaat caaatcatct tccaagagtg cctgaagtcc aggtgttcc attgttagga    180
aatctgttac aattgaagga gaaaaagcca tacatgactt ttacgagatg ggcagcgaca    240
tatggaccta tctatagtat caaaactggg gctacaagta tggttgtggt atcatctaat    300
gagatagcca aggaggcatt ggtgaccaga ttccaatcca tatctacaag gaacttatct    360
aaagccctga agtacttac agcagataag acaatggtcg caatgtcaga ttatgatgat    420
tatcataaaa cagttaagag acacatactg accgccgtct ggtgtcctaa tgcacagaaa    480
aagcatagaa ttcacagaga tatcatgatg gataacatat ctactcaact tcatgaattc    540
gtgaaaaaca acccagaaca ggaagaggta gaccttagaa aatctttca atctgagtta    600
ttcggcttag ctatgagaca agccttagga aaggatgttg aaagtttgta cgttgaagac    660
ctgaaaatca ctatgaatag agacgaaatc tttcaagtcc ttgttgttga tccaatgatg    720
ggagcaatcg atgttgattg gagagacttc tttccatacc taaagtgggt cccaaacaaa    780
aagttcgaaa atactattca acaaatgtac atcagaagag aagctgttat gaaatcttta    840
atcaaagagc acaaaaagag aatagcgtca ggcgaaaagc taaatagtta tatcgattac    900
cttttatctg aagctcaaac tttaaccgat cagcaactat tgatgtcctt gtgggaacca    960
atcattgaat cttcagatac aacaatggtc acaacagaat gggcaatgta cgaattagct   1020
aaaaacccta aattgcaaga taggttgtac agagacatta gtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag gaatggaacc agaaagatt catgaaagag   1320
aatgagacaa ttgattttca aaagacgatg gccttcggtg gtggtaagag agtttgtgct   1380
ggttccttgc aagcccttttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                       1542
```

<210> SEQ ID NO 5
<211> LENGTH: 513
<212> TYPE: PRT
<213> ORGANISM: Stevia rebaudiana

<400> SEQUENCE: 5

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
             20                  25                  30

Leu Lys Ser Tyr Thr Ser Ala Arg Arg Ser Gln Ser Asn His Leu Pro
 35                  40                  45

Arg Val Pro Glu Val Pro Gly Val Pro Leu Leu Gly Asn Leu Leu Gln
             50                  55                  60

Leu Lys Glu Lys Lys Pro Tyr Met Thr Phe Thr Arg Trp Ala Ala Thr
 65                  70                  75                  80

Tyr Gly Pro Ile Tyr Ser Ile Lys Thr Gly Ala Thr Ser Met Val Val
                 85                  90                  95

Val Ser Ser Asn Glu Ile Ala Lys Glu Ala Leu Val Thr Arg Phe Gln
             100                 105                 110

Ser Ile Ser Thr Arg Asn Leu Ser Lys Ala Leu Lys Val Leu Thr Ala
         115                 120                 125

Asp Lys Thr Met Val Ala Met Ser Asp Tyr Asp Tyr His Lys Thr
 130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                 165                 170                 175

Leu His Glu Phe Val Lys Asn Asn Pro Glu Gln Glu Val Asp Leu
     180                 185                 190

Arg Lys Ile Phe Gln Ser Glu Leu Phe Gly Leu Ala Met Arg Gln Ala
         195                 200                 205

Leu Gly Lys Asp Val Glu Ser Leu Tyr Val Glu Asp Leu Lys Ile Thr
     210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                 245                 250                 255

Val Pro Asn Lys Lys Phe Glu Asn Thr Ile Gln Gln Met Tyr Ile Arg
             260                 265                 270

Arg Glu Ala Val Met Lys Ser Leu Ile Lys Glu His Lys Lys Arg Ile
         275                 280                 285

Ala Ser Gly Glu Lys Leu Asn Ser Tyr Ile Asp Tyr Leu Leu Ser Glu
     290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                 325                 330                 335

Tyr Glu Leu Ala Lys Asn Pro Lys Leu Gln Asp Arg Leu Tyr Arg Asp
             340                 345                 350

Ile Lys Ser Val Cys Gly Ser Glu Lys Ile Thr Glu Glu His Leu Ser
         355                 360                 365

Gln Leu Pro Tyr Ile Thr Ala Ile Phe His Glu Thr Leu Arg Arg His
     370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                 405                 410                 415

Tyr Gly Cys Asn Met Asp Lys Asn Val Trp Glu Asn Pro Glu Glu Trp
             420                 425                 430

```
Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
                500                 505                 510

Ile

<210> SEQ ID NO 6
<211> LENGTH: 480
<212> TYPE: DNA
<213> ORGANISM: Arabidopsis thaliana

<400> SEQUENCE: 6
atgtcttcct cttcctcttc cagtacctct atgattgatt tgatggctgc tattattaaa      60
ggtgaaccag ttatcgtctc cgacccagca aatgcctctg cttatgaatc agttgctgca     120
gaattgtctt caatgttgat cgaaaacaga caattcgcca tgatcgtaac tacatcaatc     180
gctgttttga tcggttgtat tgtcatgttg gtatggagaa gatccggtag tggtaattct     240
aaaagagtcg aacctttgaa accattagta attaagccaa gagaagaaga aatagatgac     300
ggtagaaaga aagttacaat atttttcggt acccaaactg gtacagctga aggttttgca     360
aaagccttag gtgaagaagc taaggcaaga tacgaaaaga ctagattcaa gatagtcgat     420
ttggatgact atgccgctga tgacgatgaa tacgaagaaa agttgaagaa agaagatgtt     480

<210> SEQ ID NO 7
<211> LENGTH: 712
<212> TYPE: PRT
<213> ORGANISM: Arabidopsis thaliana

<400> SEQUENCE: 7

Met Ser Ser Ser Ser Ser Ser Thr Ser Met Ile Asp Leu Met Ala
1                 5                  10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160
```

```
Ala Phe Phe Phe Leu Ala Thr Tyr Gly Asp Gly Glu Pro Thr Asp Asn
                165                 170                 175
Ala Ala Arg Phe Tyr Lys Trp Phe Thr Glu Gly Asn Asp Arg Gly Glu
            180                 185                 190
Trp Leu Lys Asn Leu Lys Tyr Gly Val Phe Gly Leu Gly Asn Arg Gln
        195                 200                 205
Tyr Glu His Phe Asn Lys Val Ala Lys Val Val Asp Asp Ile Leu Val
    210                 215                 220
Glu Gln Gly Ala Gln Arg Leu Val Gln Val Gly Leu Gly Asp Asp Asp
225                 230                 235                 240
Gln Cys Ile Glu Asp Asp Phe Thr Ala Trp Arg Glu Ala Leu Trp Pro
                245                 250                 255
Glu Leu Asp Thr Ile Leu Arg Glu Gly Asp Thr Ala Val Ala Thr
            260                 265                 270
Pro Tyr Thr Ala Ala Val Leu Glu Tyr Arg Val Ser Ile His Asp Ser
        275                 280                 285
Glu Asp Ala Lys Phe Asn Asp Ile Thr Leu Ala Asn Gly Asn Gly Tyr
    290                 295                 300
Thr Val Phe Asp Ala Gln His Pro Tyr Lys Ala Asn Val Ala Val Lys
305                 310                 315                 320
Arg Glu Leu His Thr Pro Glu Ser Asp Arg Ser Cys Ile His Leu Glu
                325                 330                 335
Phe Asp Ile Ala Gly Ser Gly Leu Thr Met Lys Leu Gly Asp His Val
            340                 345                 350
Gly Val Leu Cys Asp Asn Leu Ser Glu Thr Val Asp Glu Ala Leu Arg
        355                 360                 365
Leu Leu Asp Met Ser Pro Asp Thr Tyr Phe Ser Leu His Ala Glu Lys
    370                 375                 380
Glu Asp Gly Thr Pro Ile Ser Ser Ser Leu Pro Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala Ala His Ala Ser Asp Pro
            420                 425                 430
Thr Glu Ala Glu Arg Leu Lys His Leu Ala Ser Pro Ala Gly Lys Asp
        435                 440                 445
Glu Tyr Ser Lys Trp Val Val Glu Ser Gln Arg Ser Leu Leu Glu Val
    450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
            500                 505                 510
Glu Lys Met Pro Thr Gly Arg Ile His Lys Gly Val Cys Ser Thr Trp
        515                 520                 525
Met Lys Asn Ala Val Pro Tyr Glu Lys Ser Glu Lys Leu Phe Leu Gly
    530                 535                 540
Arg Pro Ile Phe Val Arg Gln Ser Asn Phe Lys Leu Pro Ser Asp Ser
545                 550                 555                 560
Lys Val Pro Ile Ile Met Ile Gly Pro Gly Thr Gly Leu Ala Pro Phe
                565                 570                 575
Arg Gly Phe Leu Gln Glu Arg Leu Ala Leu Val Glu Ser Gly Val Glu
```

```
                     580                 585                 590
Leu Gly Pro Ser Val Leu Phe Phe Gly Cys Arg Asn Arg Arg Met Asp
            595                 600                 605

Phe Ile Tyr Glu Glu Glu Leu Gln Arg Phe Val Glu Ser Gly Ala Leu
            610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
            675                 680                 685

Met Asp Ser Thr Lys Ala Glu Gly Phe Val Lys Asn Leu Gln Thr Ser
            690                 695                 700

Gly Arg Tyr Leu Arg Asp Val Trp
705                 710
```

<210> SEQ ID NO 8
<211> LENGTH: 462
<212> TYPE: PRT
<213> ORGANISM: Oryza sativa

<400> SEQUENCE: 8

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
            165                 170                 175

Gln Gly Arg Pro Ala Ala Ala Pro Thr Phe Glu Val Ala Arg Met Lys
        180                 185                 190

Leu Ile Arg Thr Lys Gly Ser Ser Gly Met Ser Leu Ala Glu Arg Phe
            195                 200                 205

Ser Leu Thr Leu Ser Arg Ser Ser Leu Val Val Gly Arg Ser Cys Val
        210                 215                 220

Glu Phe Glu Pro Glu Thr Val Pro Leu Leu Ser Thr Leu Arg Gly Lys
225                 230                 235                 240
```

Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
        260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
        290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
    450                 455                 460

<210> SEQ ID NO 9
<211> LENGTH: 1503
<212> TYPE: DNA
<213> ORGANISM: Artificial Sequence
<220> FEATURE:
<223> OTHER INFORMATION: Codono-optimixed Stevia rebaudioan KAHe1

<400> SEQUENCE: 9
atggaagcct cttacctata catttctatt ttgcttttac tggcatcata cctgttcacc      60
actcaactta aaggaagag cgctaatcta ccaccaaccg tgtttccatc aataccaatc      120
attggacact atacttact caaaaagcct ctttatagaa ctttagcaaa aattgccgct      180
aagtacggac caatactgca attacaactc ggctacagac gtgttctggt gatttcctca      240
ccatcagcag cagaagagtg ctttaccaat aacgatgtaa tcttcgcaaa tagacctaag      300
acattgtttg gcaaaatagt gggtggaaca tcccttggca gtttatccta cggcgatcaa      360
tggcgtaatc taaggagagt agcttctatc gaaatcctat cagttcatag gttgaacgaa      420
tttcatgata tcagagtgga tgagaacaga ttgttaatta gaaaacttag aagttcatct      480
tctcctgtta ctcttataac agtcttttat gctctaacat gaacgtcat tatgagaatg      540 atctctggca aagatatttt cgacagtggg atagagaat tggaggagga aggtaagaga      600
tttcgagaaa tcttagacga aacgttgctt ctagccggtg cttctaatgt tggcgactac      660
ttaccaatat tgaactggtt gggagttaag tctcttgaaa agaaattgat cgctttgcag      720
aaaaagagag atgactttt ccagggttttg attgaacagg ttagaaaatc tcgtggtgct      780
aaagtaggca aggtagaaa aacgatgatc gaactcttat tatctttgca agagtcagaa      840

-continued

```
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg taataacag attgattgac     1020 gagtcagaca ttggaaatat cccttacatc gggtgtatta tcaatgaaac tctaagactc    1080
tatccagcag ggccattgtt gttcccacat gaaagttctg ccgactgcgt tatttccggt    1140
tacaatatac ctagaggtac aatgttaatc gtaaaccaat gggcgattca tcacgatcct    1200
aaagtctggg atgatcctga aacctttaaa cctgaaagat ttcaaggatt agaaggaact    1260
agagatggtt tcaaacttat gccattcggt tctgggagaa gaggatgtcc aggtgaaggt    1320
ttggcaataa ggctgttagg gatgacacta ggctcagtga tccaatgttt tgattgggag    1380
agagtaggag atgagatggt tgacatgaca gaaggtttgg gtgtcacact tcctaaggcc    1440
gttccattag ttgccaaatg taagccacgt tccgaaatga ctaatctcct atccgaactt    1500
taa                                                                  1503
```

<210> SEQ ID NO 10
<211> LENGTH: 500
<212> TYPE: PRT
<213> ORGANISM: Stevia rebaudiana

<400> SEQUENCE: 10

```
Met Glu Ala Ser Tyr Leu Tyr Ile Ser Ile Leu Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Ile Gly His Leu Tyr Leu Leu Lys
        35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
    130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
    210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
```

```
                    245                 250                 255
Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
    290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
    370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
    450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
        500

<210> SEQ ID NO 11
<211> LENGTH: 2124
<212> TYPE: DNA
<213> ORGANISM: Stevia rebaudiana

<400> SEQUENCE: 11
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca aacgtcggt tgctgtattg      180 atcggatgcg ttgtcgtttt ggtgtggcgg agatcgtcta cgaagaagtc ggcgttggag     240
ccaccggtga ttgtggttcc gaagagagtg caagaggagg aagttgatga tggtaagaag     300
aaagttacgg ttttcttcgg cacccaaact ggaacagctg aaggcttcgc taaggcactt     360
gttgaggaag ctaaagctcg atatgaaaag gctgtcttta agtaattga tttggatgat     420 tatgctgctg atgacgatga gtatgaggag aaactaaaga agaatctttt ggcctttttc     480
tttttggcta cgtatggaga tggtgagcca acagataatg ctgccagatt ttataaatgg     540
tttactgagg gagatgcgaa aggagaatgg cttaataagc ttcaatatgg agtatttggt     600
ttgggtaaca gacaatatga acattttaac aagatcgcaa aagtggttga tgatggtctt     660
```

```
gtagaacagg gtgcaaagcg tcttgttcct gttggacttg gagatgatga tcaatgtatt      720
gaagatgact tcaccgcatg gaaagagtta gtatggccgg agttggatca attacttcgt      780
gatgaggatg acacaactgt tgctactcca tacacagctg ctgttgcaga atatcgcgtt      840
gttttcatg aaaaaccaga cgcgcttcct gaagattata gttatacaaa tggccatgct       900
gttcatgatg ctcaacatcc atgcagatcc aacgtggctg tcaaaaagga acttcatagt      960
cctgaatctg accggtcttg cactcatctt gaatttgaca tctcgaacac cggactatca      1020
tatgaaactg gggaccatgt tggagtttac tgtgaaaact tgagtgaagt tgtgaatgat      1080
gctgaaagat tagtaggatt accaccagac acttactcct ccatccacac tgatagtgaa      1140
gacgggtcgc cacttggcgg agcctcattg ccgcctcctt tcccgccatg cactttaagg      1200
aaagcattga cgtgttatgc tgatgttttg agttctccca agaagtcggc tttgcttgca      1260
ctagctgctc atgccaccga tcccagtgaa gctgatagat tgaaatttct tgcatccccc      1320
gccggaaagg atgaatattc tcaatggata gttgcaagcc aaagaagtct ccttgaagtc      1380
atggaagcat tcccgtcagc taagccttca cttggtgttt tctttgcatc tgttgccccg      1440
cgcttacaac aagatacta ctctatttct tcctcaccca agatggcacc ggataggatt       1500
catgttacat gtgcattagt ctatgagaaa acacctgcag ccgcatccca caaaggagtt      1560
tgttcaactt ggatgaagaa cgcagtgcct atgaccgaga gtcaagattg cagttgggcc      1620
ccaatatacg tccgaacatc caatttcaga ctaccatctg accctaaggt cccggttatc      1680
atgattggac ctggcactgg tttggctcct tttagaggtt tccttcaaga gcggttagct      1740
ttaaaggaag ccggaactga cctcggttta tccattttat tcttcggatg taggaatcgc      1800
aaagtggatt tcatatatga aaacgagctt aacaactttg tggagactgg tgctctttct      1860
gagcttattg ttgctttctc ccgtgaaggc ccgactaagg aatatgtgca acacaagatg      1920
agtgagaagg cttcggatat ctggaacttg ctttctgaag gagcatattt atacgtatgt      1980
ggtgatgcca aaggcatggc caaagatgta catcgaaccc tccacacaat tgtgcaagaa      2040
cagggatctc ttgactcgtc aaaggcagaa ctctacgtga agaatctaca aatgtcagga      2100
agatacctcc gtgacgtttg gtaa                                             2124

<210> SEQ ID NO 12
<211> LENGTH: 707
<212> TYPE: PRT
<213> ORGANISM: Stevia rebaudiana

<400> SEQUENCE: 12

Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Glu Val Asp
                85                  90                  95

Asp Gly Lys Lys Lys Val Thr Val Phe Phe Gly Thr Gln Thr Gly Thr
            100                 105                 110
```

```
Ala Glu Gly Phe Ala Lys Ala Leu Val Glu Ala Lys Ala Arg Tyr
            115                 120                 125

Glu Lys Ala Val Phe Lys Val Ile Asp Leu Asp Tyr Ala Ala Asp
        130                 135                 140

Asp Asp Glu Tyr Glu Lys Leu Lys Lys Glu Ser Leu Ala Phe Phe
145                 150                 155                 160

Phe Leu Ala Thr Tyr Gly Asp Gly Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
            195                 200                 205

Phe Asn Lys Ile Ala Lys Val Val Asp Asp Gly Leu Val Glu Gln Gly
        210                 215                 220

Ala Lys Arg Leu Val Pro Val Gly Leu Gly Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
            260                 265                 270

Ala Ala Val Ala Glu Tyr Arg Val Val Phe His Glu Lys Pro Asp Ala
            275                 280                 285

Leu Ser Glu Asp Tyr Ser Tyr Thr Asn Gly His Ala Val His Asp Ala
        290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
        515                 520                 525
```

-continued

Val Pro Met Thr Glu Ser Gln Asp Cys Ser Trp Ala Pro Ile Tyr Val
    530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
            580                 585                 590

Leu Phe Phe Gly Cys Arg Asn Arg Lys Val Asp Phe Ile Tyr Glu Asn
                595                 600                 605

Glu Leu Asn Asn Phe Val Glu Thr Gly Ala Leu Ser Glu Leu Ile Val
        610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
690                 695                 700

Asp Val Trp
705

<210> SEQ ID NO 13
<211> LENGTH: 481
<212> TYPE: PRT
<213> ORGANISM: Stevia rebaudiana

<400> SEQUENCE: 13

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

-continued

Lys Asp Phe Pro Leu Asp Trp Ser Thr Asp Leu Asn Asp Lys Val Leu
            195                 200                 205

Met Phe Thr Thr Glu Ala Pro Gln Arg Ser His Lys Val Ser His His
210                 215                 220

Ile Phe His Thr Phe Asp Glu Leu Pro Ser Ile Ile Lys Thr Leu
225                 230                 235                 240

Ser Leu Arg Tyr Asn His Ile Tyr Thr Ile Gly Pro Leu Gln Leu Leu
            245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
            275                 280                 285

Gln Ser Lys Glu Pro Asn Ser Val Val Tyr Val Asn Phe Gly Ser Thr
            290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
            370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
            435                 440                 445

Asp Trp Lys Glu Lys Ala Arg Ile Ala Ile Ala Pro Asn Gly Ser Ser
            450                 455                 460

Ser Leu Asn Ile Asp Lys Met Val Lys Glu Ile Thr Val Leu Ala Arg
465                 470                 475                 480

Asn

<210> SEQ ID NO 14
<211> LENGTH: 460
<212> TYPE: PRT
<213> ORGANISM: Stevia rebaudiana

<400> SEQUENCE: 14

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
        50                  55                  60

Glu Ile Gln Ala Ile Ser Asp Gly Cys Asp Glu Gly Gly Phe Met Ser
65                  70                  75                  80

```
Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 15
<211> LENGTH: 458
<212> TYPE: PRT
<213> ORGANISM: Stevia rebaudiana
```

<400> SEQUENCE: 15

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                      55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415
```

```
Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 16
<211> LENGTH: 473
<212> TYPE: PRT
<213> ORGANISM: Stevia rebaudiana

<400> SEQUENCE: 16

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
```

|  |  | 325 |  |  |  | 330 |  |  |  | 335 |  |
|---|---|---|---|---|---|---|---|---|---|---|---|
| Gly | Leu | Val | Trp | Thr | Ser | Trp | Ala | Pro | Gln | Leu | Arg | Ile | Leu | Ser | His |
|  |  |  | 340 |  |  |  | 345 |  |  |  | 350 |

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Gly
370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
            405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
            450                 455                 460

Arg Ala Val Ala Ile Asp His Glu Ser
465                 470

<210> SEQ ID NO 17
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 17

```
atggctactt ctgattccat cgttgacgat agaaagcaat tgcatgttgc tactttcca     60
tggttggctt tcggtcatat tttgccatac ttgcaattgt ccaagttgat tgctgaaaag   120
ggtcacaagg tttcattctt gtctaccacc agaaacatcc aaagattgtc ctctcatatc   180
tccccattga tcaacgttgt tcaattgact ttgccaagag tccaagaatt gccagaagat   240
gctgaagcta ctactgatgt tcatccagaa gatatccctt acttgaaaaa ggcttccgat   300
ggtttacaac cagaagttac tagattcttg aacaacatt ccccagattg gatcatctac   360
gattatactc attactggtt gccatccatt gctgcttcat gggtatttc tagagcccat   420
ttctctgtta ctactccatg ggctattgct tatatgggtc catctgctga tgctatgatt   480
aacggttctg atggtagaac taccgttgaa gatttgacta ctccaccaa gtggtttcca   540
tttccaacaa aagtctgttg agaaaaacac gatttggcta gattggttcc atacaaagct   600
ccaggtattt ctgatggtta cagaatgggt atggttttga aggttccga ttgcttgttg   660
tctaagtgct atcatgaatt cggtactcaa tggttgcctt tgttggaaac attgcatcaa   720
gttccagttg ttccagtagg tttgttgcca ccagaaattc aggtgacga aaaagacgaa   780
acttgggttt ccatcaaaaa gtggttggat ggtaagcaaa agggtctgt tgtttatgtt   840
gctttgggtt ccgaagcttt ggtttctcaa accgaagttg ttgaattggc tttgggtttg   900
gaattgtctg gtttgccatt tgtttgggct tacagaaaac ctaaaggtcc agctaagtct   960
gattctgtta attgccaga tggtttcgtt gaaagaacta gagatagagg tttggttttgg  1020
acttcttggg ctccacaatt gagaattttg tctcatgaat ccgtctgtgg tttcttgact  1080
cattgtggtt ctggttctat cgttgaaggt ttgatgtttg gtcacccatt gattatgttg  1140
ccaatctttg gtgaccaacc attgaacgct agattattgg aagataagca agtcggtatc  1200
```

-continued

| | |
|---|---|
| gaaatcccaa gaaatgaaga agatggttgc ttgaccaaag aatctgttgc tagatctttg | 1260 |
| agatccgttg tcgttgaaaa agaaggtgaa atctacaagg ctaacgctag agaattgtcc | 1320 |
| aagatctaca acgataccaa ggtcgaaaaa gaatacgttt cccaattcgt tgactacttg | 1380 |
| gaaaagaatg ctagagctgt tgccattgat catgaatctt ga | 1422 |

```
<210> SEQ ID NO 18
<211> LENGTH: 2133
<212> TYPE: DNA
<213> ORGANISM: Artificial Sequence
<220> FEATURE:
<223> OTHER INFORMATION: Codon optimized CPR

<400> SEQUENCE: 18
```

| | |
|---|---|
| atgcaatcag attcagtcaa agtctctcca tttgatttgg tttccgctgc tatgaatggc | 60 |
| aaggcaatgg aaaagttgaa cgctagtgaa tctgaagatc aacaacatt gcctgcacta | 120 |
| aagatgctag ttgaaaatag agaattgttg acactgttca caacttcctt cgcagttctt | 180 |
| attgggtgtc ttgtatttct aatgtggaga cgttcatcct ctaaaaagct ggtacaagat | 240 |
| ccagttccac aagttatcgt tgtaaagaag aaagagaagg agtcagaggt tgatgacggg | 300 |
| aaaagaaag tttctatttt ctacggcaca caaacaggac tgccgaagg ttttgctaaa | 360 |
| gcattagtcg aggaagcaaa agtgagatat gaaaagacct ctttcaaggt tatcgatcta | 420 |
| gatgactacg ctgcagatga tgatgaatat gaggaaaaac tgaaaaagga atccttagcc | 480 |
| ttcttcttct tggccacata cggtgatggt gaacctactg ataatgctgc taacttctac | 540 |
| aagtggttca cagaaggcga cgataaaggt gaatggctga aaaagttaca atacggagta | 600 |
| tttggtttag gtaacagaca atatgaacat ttcaacaaga tcgctattgt agttgatgat | 660 |
| aaacttactg aaatgggagc caaaagatta gtaccagtag attaggggga tgatgatcag | 720 |
| tgtatagaag atgacttcac cgcctggaag gaattggtat ggccagaatt ggatcaactt | 780 |
| ttaagggacg aagatgatac ttctgtgact accccataca ctgcagccgt attggagtac | 840 |
| agagtggttt accatgataa accagcagac tcatatgctg aagatcaaac ccatacaaac | 900 |
| ggtcatgttt tcatgatgc acagcatcct tcaagatcta atgtggcttt caaaaaggaa | 960 |
| ctacacacct ctcaatcaga taggtcttgt actcacttag aattcgatat ttctcacaca | 1020 |
| ggactgtctt acgaaactgg cgatcacgtt ggcgtttatt ccgagaactt gtccgaagtt | 1080 |
| gtcgatgaag cactaaaact gttagggtta tcaccagaca catacttctc agtccatgct | 1140 |
| gataaggagg atgggacacc tatcggtggt gcttcactac caccaccttt tcctccttgc | 1200 |
| acattgagag acgctctaac cagatacgca gatgtcttat cctcacctaa aaaggtagct | 1260 |
| ttgctggcat tggctgctca tgctagtgat cctagtgaag ccgataggtt aaagttcctg | 1320 |
| gcttcaccag ccggaaaaga tgaatatgca caatggatcg tcgccaacca acgttctttg | 1380 |
| ctagaagtga tgcaaagttt tccatctgcc aagcctccat taggtgtgtt cttcgcagca | 1440 |
| gtagctccac gtttacaacc aagatactac tctatcagtt catctcctaa gatgtctcct | 1500 |
| aacagaatac atgttacatg tgctttggtg tacgagacta ctccagcagg cagaattcac | 1560 |
| agaggattgt gttcaacctg gatgaaaaat gctgtccctt aacagagtc acctgattgc | 1620 |
| tctcaagcat ccattttcgt tagaacatca atttcagac ttccagtgga tccaaaagtt | 1680 |
| ccagtcatta tgataggacc aggcactggt cttgccccat tcaggggctt tcttcaagag | 1740 |
| agattggcct tgaaggaatc tggtacagaa ttgggttctt ctatctttt ctttggttgc | 1800 |
| cgtaatagaa aagttgactt tatctacgag gacgagctta caatttttgt tgagacagga | 1860 |

-continued

```
gcattgtcag aattgatcgt cgcattttca agagaaggga ctgccaaaga gtacgttcag    1920
cacaagatga gtcaaaaagc ctccgatata tggaaacttc taagtgaagg tgcctatctt    1980
tatgtctgtg gcgatgcaaa gggcatggcc aaggatgtcc atagaactct gcatacaatt    2040
gttcaggaac aagggagtct ggattcttcc aaggctgaat tgtacgtcaa aaacttacag    2100
atgtctggaa gatacttaag agatgtttgg taa                                 2133
```

<210> SEQ ID NO 19
<211> LENGTH: 709
<212> TYPE: PRT
<213> ORGANISM: Stevia rebaudiana

<400> SEQUENCE: 19

```
Gln Ser Asp Ser Val Lys Val Ser Pro Phe Asp Leu Val Ser Ala Ala
1               5                   10                  15

Met Asn Gly Lys Ala Met Glu Lys Leu Asn Ala Ser Glu Ser Glu Asp
            20                  25                  30

Pro Thr Thr Leu Pro Ala Leu Lys Met Leu Val Glu Asn Arg Glu Leu
        35                  40                  45

Leu Thr Leu Phe Thr Thr Ser Phe Ala Val Leu Ile Gly Cys Leu Val
    50                  55                  60

Phe Leu Met Trp Arg Arg Ser Ser Lys Lys Leu Val Gln Asp Pro
65                  70                  75                  80

Val Pro Gln Val Ile Val Lys Lys Glu Lys Ser Glu Val
                85                  90                  95

Asp Asp Gly Lys Lys Val Ser Ile Phe Tyr Gly Thr Gln Thr Gly
                100                 105                 110

Thr Ala Glu Gly Phe Ala Lys Ala Leu Val Glu Glu Ala Lys Val Arg
            115                 120                 125

Tyr Glu Lys Thr Ser Phe Lys Val Ile Asp Leu Asp Asp Tyr Ala Ala
        130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Asn Phe Tyr Lys Trp Phe Thr Glu Gly Asp Asp Lys Gly Glu Trp Leu
            180                 185                 190

Lys Lys Leu Gln Tyr Gly Val Phe Gly Leu Gly Asn Arg Gln Tyr Glu
        195                 200                 205

His Phe Asn Lys Ile Ala Ile Val Val Asp Asp Lys Leu Thr Glu Met
    210                 215                 220

Gly Ala Lys Arg Leu Val Pro Val Gly Leu Gly Asp Asp Gln Cys
225                 230                 235                 240

Ile Glu Asp Asp Phe Thr Ala Trp Lys Glu Leu Val Trp Pro Glu Leu
                245                 250                 255

Asp Gln Leu Leu Arg Asp Glu Asp Thr Ser Val Thr Thr Pro Tyr
            260                 265                 270

Thr Ala Ala Val Leu Glu Tyr Arg Val Val Tyr His Asp Lys Pro Ala
        275                 280                 285

Asp Ser Tyr Ala Glu Asp Gln Thr His Thr Asn Gly His Val Val His
    290                 295                 300

Asp Ala Gln His Pro Ser Arg Ser Asn Val Ala Phe Lys Lys Glu Leu
305                 310                 315                 320
```

```
His Thr Ser Gln Ser Asp Arg Ser Cys Thr His Leu Glu Phe Asp Ile
            325                 330                 335

Ser His Thr Gly Leu Ser Tyr Glu Thr Gly Asp His Val Gly Val Tyr
            340                 345                 350

Ser Glu Asn Leu Ser Glu Val Val Asp Glu Ala Leu Lys Leu Leu Gly
            355                 360                 365

Leu Ser Pro Asp Thr Tyr Phe Ser Val His Ala Asp Lys Glu Asp Gly
370                 375                 380

Thr Pro Ile Gly Gly Ala Ser Leu Pro Pro Phe Pro Pro Cys Thr
385                 390                 395                 400

Leu Arg Asp Ala Leu Thr Arg Tyr Ala Asp Val Leu Ser Ser Pro Lys
            405                 410                 415

Lys Val Ala Leu Leu Ala Leu Ala Ala His Ala Ser Asp Pro Ser Glu
            420                 425                 430

Ala Asp Arg Leu Lys Phe Leu Ala Ser Pro Ala Gly Lys Asp Glu Tyr
            435                 440                 445

Ala Gln Trp Ile Val Ala Asn Gln Arg Ser Leu Leu Glu Val Met Gln
            450                 455                 460

Ser Phe Pro Ser Ala Lys Pro Pro Leu Gly Val Phe Phe Ala Ala Val
465                 470                 475                 480

Ala Pro Arg Leu Gln Pro Arg Tyr Tyr Ser Ile Ser Ser Ser Pro Lys
            485                 490                 495

Met Ser Pro Asn Arg Ile His Val Thr Cys Ala Leu Val Tyr Glu Thr
            500                 505                 510

Thr Pro Ala Gly Arg Ile His Arg Gly Leu Cys Ser Thr Trp Met Lys
            515                 520                 525

Asn Ala Val Pro Leu Thr Glu Ser Pro Asp Cys Ser Gln Ala Ser Ile
            530                 535                 540

Phe Val Arg Thr Ser Asn Phe Arg Leu Pro Val Asp Pro Lys Val Pro
545                 550                 555                 560

Val Ile Met Ile Gly Pro Gly Thr Gly Leu Ala Pro Phe Arg Gly Phe
            565                 570                 575

Leu Gln Glu Arg Leu Ala Leu Lys Glu Ser Gly Thr Glu Leu Gly Ser
            580                 585                 590

Ser Ile Phe Phe Phe Gly Cys Arg Asn Arg Lys Val Asp Phe Ile Tyr
            595                 600                 605

Glu Asp Glu Leu Asn Asn Phe Val Glu Thr Gly Ala Leu Ser Glu Leu
            610                 615                 620

Ile Val Ala Phe Ser Arg Glu Gly Thr Ala Lys Glu Tyr Val Gln His
625                 630                 635                 640

Lys Met Ser Gln Lys Ala Ser Asp Ile Trp Lys Leu Leu Ser Glu Gly
            645                 650                 655

Ala Tyr Leu Tyr Val Cys Gly Asp Ala Lys Gly Met Ala Lys Asp Val
            660                 665                 670

His Arg Thr Leu His Thr Ile Val Gln Glu Gln Gly Ser Leu Asp Ser
            675                 680                 685

Ser Lys Ala Glu Leu Tyr Val Lys Asn Leu Gln Met Ser Gly Arg Tyr
            690                 695                 700

Leu Arg Asp Val Trp
705
```